US012646595B2

(12) United States Patent
Lewis et al.

(10) Patent No.: US 12,646,595 B2
(45) Date of Patent: Jun. 2, 2026

(54) COMPUTER-BASED SYSTEMS CONFIGURED FOR REAL-TIME INTEGRATION OF RESOURCES ACROSS DISPARATE ELECTRONIC PLATFORMS AND METHODS OF USE THEREOF

(71) Applicant: R1 RCM Inc., Murray, UT (US)

(72) Inventors: Michael Lewis, Murray, UT (US);
James Grove, Murray, UT (US);
Mercy Murguia Rosales, Murray, UT (US); Wayne Delisser, Murray, UT (US)

(73) Assignee: R1 RCM INC., Murray, UT (US)

( * ) Notice: Subject to any disclaimer, the term of this patent is extended or adjusted under 35 U.S.C. 154(b) by 323 days.

(21) Appl. No.: 18/419,772

(22) Filed: Jan. 23, 2024

(65) Prior Publication Data

US 2024/0412827 A1    Dec. 12, 2024

Related U.S. Application Data

(63) Continuation of application No. 18/332,555, filed on Jun. 9, 2023, now Pat. No. 11,887,702.

(51) Int. Cl.
G16H 10/20      (2018.01)
G06F 9/50       (2006.01)
               (Continued)

(52) U.S. Cl.
CPC ........... G16H 10/20 (2018.01); G06F 9/5055 (2013.01); G06F 9/548 (2013.01);
               (Continued)

(58) Field of Classification Search
CPC ........ G16H 10/20; G16H 10/60; G06F 16/27; G06F 16/24539; G06F 16/2457; G06F 9/5055; G06F 9/548
See application file for complete search history.

(56) References Cited

U.S. PATENT DOCUMENTS 10,255,996 B2    4/2019  Ivanoff et al.
10,326,670 B2    6/2019  Sharma et al.
               (Continued)

FOREIGN PATENT DOCUMENTS

WO        2016043798 A1      3/2016

OTHER PUBLICATIONS

M. J. H. Faruk, A. J. Patinga, L. Migiro, H. Shahriar and S. Sneha, "Leveraging Healthcare API to transform Interoperability: API Security and Privacy," 2022 IEEE 46th Annual Computers, Software, and Applications Conference (COMPSAC), Los Alamitos, CA, USA, 2022, pp. 444-445 (Year: 2022).*
               (Continued)

*Primary Examiner* — Fonya M Long
*Assistant Examiner* — Anthony Balaj
(74) *Attorney, Agent, or Firm* — Greenberg Traurig, LLP

(57)              ABSTRACT

Described herein are systems and methods for real-time integration of resources across disparate electronic platforms, including automated data mapping and message translation for improved resource platform access. The embodiments provide technical solutions and technical improvements that overcome technical problems, drawbacks and/or deficiencies in the technical fields involving compatibility with multiple third-party APIs, unified access to data from multiple platforms, and efficient synchronization with multiple platforms. Technical solutions and technical improvements herein include aspects of improved API call normalization for scalable and flexible API calls that integrate with various platforms, proactive and/or real-time caching of data associated with the various platforms, and efficient orchestration of client queries, platform API calls and cache querying to answer the client queries most efficiently and quickly with up-to-date, synchronized data.

20 Claims, 12 Drawing Sheets

(51) Int. Cl.

| | |
|---|---|
| *G06F 9/54* | (2006.01) |
| *G06F 16/2453* | (2019.01) |
| *G06F 16/2457* | (2019.01) |
| *G06F 16/27* | (2019.01) |
| *G16H 10/60* | (2018.01) |

(52) U.S. Cl.
CPC .... *G06F 16/24539* (2019.01); *G06F 16/2457* (2019.01); *G06F 16/27* (2019.01); *G16H 10/60* (2018.01)

(56) References Cited

U.S. PATENT DOCUMENTS

| | | | | |
|---|---|---|---|---|
| 10,909,985 | B1 * | 2/2021 | Whittenburg | G10L 15/30 |
| 11,397,594 | B1 * | 7/2022 | David | G06F 9/44526 |
| 2006/0026051 | A1 | 2/2006 | Rose | |
| 2010/0228564 | A1 | 9/2010 | Kharraz Tavakol et al. | |
| 2015/0019480 | A1 * | 1/2015 | Maquaire | G06F 16/2365 |
| | | | | 707/609 |
| 2017/0262591 | A1 * | 9/2017 | Canning | G06Q 10/063114 |
| 2017/0270532 | A1 * | 9/2017 | Livesay | G16H 10/60 |
| 2020/0279343 | A1 | 9/2020 | Kharraz-Tavakol | |
| 2022/0038430 | A1 * | 2/2022 | Fagan | H04L 63/0272 |
| 2022/0210010 | A1 * | 6/2022 | Ritchie | H04L 41/022 |
| 2023/0018265 | A1 | 1/2023 | Feuerstein | |
| 2023/0030187 | A1 | 2/2023 | Shankar et al. | |
| 2023/0162844 | A1 | 5/2023 | Lau et al. | |
| 2024/0070146 | A1 * | 2/2024 | Khalyknazarov | G06F 16/2386 |

OTHER PUBLICATIONS

Kahn, M.A., A methodology for rapid deployment of shared cohort discovery system with integrated EHR to enable federated health data governance, ProQuest Dissertations and Theses Professional (2018).

Faruk, et al., "Leveraging Healthcare API to transform Interoperability: API Security and Privacy," 2022 IEEE 46th Annual Computers, Software, and Applications Conference (COMPSAC), Los Alamitos, CA, USA, pp. 444-445 (2022).

* cited by examiner

COMPUTER-BASED SYSTEMS CONFIGURED FOR REAL-TIME INTEGRATION OF RESOURCES ACROSS DISPARATE ELECTRONIC PLATFORMS AND METHODS OF USE THEREOF

RELATED APPLICATION DATA

This application is a continuation of and claims priority to co-pending U.S. patent application Ser. No. 18/332,555, filed Jun. 9, 2023, entitled COMPUTER-BASED SYSTEMS CONFIGURED FOR REAL-TIME INTEGRATION OF RESOURCES ACROSS DISPARATE ELECTRONIC PLATFORMS AND METHODS OF USE THEREOF, which is incorporated herein by reference in its entirety, for all purposes.

FIELD OF TECHNOLOGY

The present disclosure generally relates to computer-based systems and methods for real-time integration of resources across disparate electronic platforms, including automated data mapping and message translation for improved resource platform access.

BACKGROUND OF TECHNOLOGY

Typically, integration with one or more platforms involves adding an application programming interface (API) or other interface technology specific to each platform being integrated. In the context of a cloud or internet-based platform, such integrations can result in many different APIs, each of which having system-specific structures and fields. As a result, access to data provided by the platform typically requires a client or front-end to construct system-specific queries.

SUMMARY OF DESCRIBED SUBJECT MATTER

In some embodiments, the present disclosure provides an exemplary technically improved computer-based system/ method/apparatus that includes at least the following components/steps.

In some aspects, the techniques described herein relate to a system including: at least one interface gateway configured to interface with at least one client device and a plurality of resource platforms, the at least one interface gateway including a resource orchestrator including at least one processor in communication with at least one non-transitory computer-readable medium having software instructions stored thereon, wherein, upon execution of the software instructions, the at least one processor is configured to: generate an abstracted query about a plurality of resources managed by the plurality of resource platforms; wherein the abstracted query is for at least: each respective resource of the plurality of resources, an availability of each respective resource of the plurality of resources, and a capability of each respective resource of the plurality of resources; identify a plurality of application programming interfaces maintained by a normalization layer for querying the plurality of resource platforms about the plurality of resources managed by the plurality of resource platforms; wherein the plurality of application programming interfaces are defined by a plurality of resource selection questionnaire templates specific to each respective resource platform of the plurality of resource platforms; generate a respective normalized application programming interface call to each respective resource platform by modifying the abstracted query for each respective resource platform of the plurality of resource platforms based on each respective application programming interface of the plurality of application programming interfaces; store, responsive to the respective normalized application programming interface call to each of the plurality of resource platforms, in a resource cache, a plurality of resource objects for each resource platform, wherein each of the plurality of resource objects that represent a respective resource of the plurality of resources managed by the plurality of resource platforms include: an availability property indicating the availability of the respective resource, and a capability property indicating the capability of the respective resource; receive, from the at least one client device, a resource request representing at least one request for at least one resource of the plurality of resources; wherein the resource request includes: at least one user attribute associated with a user, and at least one resource request attribute defining at least one requested capability; access the resource cache including the plurality of resource objects representing the plurality of resources managed by the plurality of resource platforms; determine at least one particular resource property representing at least one particular capability that corresponds to: the at least one user attribute, and the at least one requested capability defined by the at least one resource request attribute; determine a particular resource object of the plurality of resource objects in the resource cache, the particular resource object including at least one particular capability property; wherein the particular resource object represents a particular resource for the resource request; determine a particular resource platform associated with the particular resource object; transmit to the at least one client device, in real-time, a particular plurality of resource selection questionnaire templates specific to the particular resource platform so as to enable the at least one client device to: display the particular plurality of resource selection questionnaire templates, and return at least one user input associated with the particular plurality of resource selection questionnaire templates; determine, based on the at least one user input, a particular availability of the particular resource object; and generate, based on a particular application programming interface of the particular resource platform and the particular availability of the particular resource object, a particular application programming interface call including at least one resource selection configured to cause the particular resource platform to secure, for the user, the at least one resource associated with the particular resource object.

In some aspects, the techniques described herein relate to a system, wherein identifying the plurality of application programming interfaces includes identifying three application programming interfaces for each of the plurality of resource platforms.

In some aspects, the techniques described herein relate to a system, wherein storing the plurality of resource objects includes: receive, responsive to the respective normalized application programming interface call to each of the plurality of resource platforms, an unstructured response from each of the plurality of resource platforms, wherein the unstructured response is indicative of at least: the respective resource, the availability of the respective resource, and the capability of the respective resource; and generate, based on respective mapping identifiers for each respective resource platform of the plurality of resource platforms, the plurality of resource objects for storage in the resource cache using the respective mapping identifiers to map the unstructured response to the plurality of resource objects, wherein each of the plurality of resource objects that represent the plurality of resources managed by the plurality of resource platforms include: a respective resource property mapped to the respective resource, the availability property mapped to the availability of the respective resource, and the capability property mapped to the capability of the respective resource.

In some aspects, the techniques described herein relate to a system, wherein the at least one processor is further configured to: determine, for each resource platform, the plurality of resource objects associated with the abstracted query based at least in part on the respective mapping identifiers; determine a set of additional application programming interface fields in each respective normalized application programming interface call; wherein the set of additional application programming interface fields are in addition to a set of abstracted query fields of the abstracted query; wherein the set of abstracted query fields define each respective resource of the plurality of resources; determine a set of additional application programming interface data for each respective normalized application programming interface call to populate the set of additional application programming interface fields based at least in part on the plurality of resource objects associated with the abstracted query; and generate the respective normalized application programming interface call to each respective resource platform by modifying the abstracted query for each respective resource platform of the plurality of resource platforms to include the set of additional application programming interface fields including the set of additional application programming interface data of each respective normalized application programming interface call.

In some aspects, the techniques described herein relate to a system, wherein the at least one processor is further configured to: generate, periodically for each resource platform of the plurality of resource platforms, according to at least one refresh period, at least one subsequent abstracted query configured to synchronize the plurality of resource objects with the plurality of resource platforms; generate, based on the at least one refresh period, at least one subsequent respective normalized application programming interface call to each respective resource platform by modifying the at least one subsequent abstracted query for each respective resource platform of the plurality of resource platforms based on each respective application programming interface of the plurality of application programming interfaces; and storing, responsive to the at least one subsequent respective normalized application programming interface call to each of the plurality of resource platforms, in the resource cache, a plurality of refreshed resource objects for each resource platform, wherein the plurality of refreshed resource objects includes an up-to-date record of each resource of the plurality of resources managed by the plurality of resource platforms, including: an updated availability property indicating a current availability of the respective resource, and an updated capability property indicating a current capability of the respective resource.

In some aspects, the techniques described herein relate to a system, wherein the at least one refresh period includes one day.

In some aspects, the techniques described herein relate to a system, wherein the plurality of refreshed resource objects includes the up-to-date record for changed resources of the plurality of resources.

In some aspects, the techniques described herein relate to a system, wherein the plurality of refreshed resource objects includes the up-to-date record for all the plurality of resources.

In some aspects, the techniques described herein relate to a system, wherein the plurality of resource platforms includes a plurality of electronic health record (EHR) integrations.

In some aspects, the techniques described herein relate to a system, wherein the plurality of resources includes a plurality of healthcare providers.

In some aspects, the techniques described herein relate to a method including: generating, by at least one processor of a resource orchestrator of at least one interface gateway configured to interface with at least one client device and a plurality of resource platforms, an abstracted query about a plurality of resources managed by the plurality of resource platforms; wherein the abstracted query is for at least: each respective resource of the plurality of resources, an availability of each respective resource of the plurality of resources, and a capability of each respective resource of the plurality of resources; identifying, by the at least one processor, a plurality of application programming interfaces maintained by a normalization layer for querying the plurality of resource platforms about the plurality of resources managed by the plurality of resource platforms; wherein the plurality of application programming interfaces are defined by a plurality of resource selection questionnaire templates specific to each respective resource platform of the plurality of resource platforms; generating, by the at least one processor, a respective normalized application programming interface call to each respective resource platform by modifying the abstracted query for each respective resource platform of the plurality of resource platforms based on each respective application programming interface of the plurality of application programming interfaces; storing, by the at least one processor, responsive to the respective normalized application programming interface call to each of the plurality of resource platforms, in a resource cache, a plurality of resource objects for each resource platform, wherein each of the plurality of resource objects that represent a respective resource of the plurality of resources managed by the plurality of resource platforms include: an availability property indicating the availability of the respective resource, and a capability property indicating the capability of the respective resource; receiving, by the at least one processor, from the at least one client device, a resource request representing at least one request for at least one resource of the plurality of resources; wherein the resource request includes: at least one user attribute associated with a user, and at least one resource request attribute defining at least one requested capability; accessing, by the at least one processor, the resource cache including the plurality of resource objects representing the plurality of resources managed by the plurality of resource platforms; determining, by the at least one processor, at least one particular resource attribute representing at least one particular capability that corresponds to: the at least one user attribute, and the at least one requested capability defined by the at least one resource request attribute; determining, by the at least one processor, a particular resource object of the plurality of resource objects in the resource cache, the particular resource object including at least one particular capability property; wherein the particular resource object represents a particular resource for the resource request; determining, by the at least one processor, a particular resource platform associated with the particular resource object; transmit to the at least one client device, in real-time, a particular plurality of resource selection questionnaire templates specific to the particular resource platform so as to enable the at least one client device to: display the particular plurality of resource selection questionnaire templates, and return, to the at least one processor, at least one user input associated with the particular plurality of resource selection questionnaire templates; determining, by the at least one processor, based on the at least one user input, a particular availability of the particular resource object; and generating, by the at least one processor, based on a particular application programming interface of the particular resource platform and the particular availability of the particular resource object, a particular application programming interface call including at least one resource selection configured to cause the particular resource platform to secure, for the user, the at least one resource associated with the particular resource object.

In some aspects, the techniques described herein relate to a method, wherein identifying the plurality of application programming interfaces includes identifying three application programming interfaces for each of the plurality of resource platforms.

In some aspects, the techniques described herein relate to a method, wherein storing the plurality of resource objects includes: receiving, by the at least one processor, responsive to the respective normalized application programming interface call to each of the plurality of resource platforms, an unstructured response from each of the plurality of resource platforms, wherein the unstructured response is indicative of at least: the respective resource, the availability of the respective resource, and the capability of the respective resource; and generating, by the at least one processor, based on respective mapping identifiers for each respective resource platform of the plurality of resource platforms, the plurality of resource objects for storage in the resource cache using the respective mapping identifiers to map the unstructured response to the plurality of resource objects, wherein each of the plurality of resource objects that represent the plurality of resources managed by the plurality of resource platforms include: a respective resource property mapped to the respective resource, the availability property mapped to the availability of the respective resource, and the capability property mapped to the capability of the respective resource.

In some aspects, the techniques described herein relate to a method, further including: determining, by the at least one processor, for each resource platform, the plurality of resource objects associated with the abstracted query based at least in part on the respective mapping identifiers; determining, by the at least one processor, a set of additional application programming interface fields in each respective normalized application programming interface call; wherein the set of additional application programming interface fields are in addition to a set of abstracted query fields of the abstracted query; wherein the set of abstracted query fields define each respective resource of the plurality of resources; determining, by the at least one processor, a set of additional application programming interface data for each respective normalized application programming interface call to populate the set of additional application programming interface fields based at least in part on the plurality of resource objects associated with the abstracted query; and generating, by the at least one processor, the respective normalized application programming interface call to each respective resource platform by modifying the abstracted query for each respective resource platform of the plurality of resource platforms to include the set of additional application programming interface fields including the set of additional application programming interface data of each respective normalized application programming interface call.

In some aspects, the techniques described herein relate to a method, further including: generating, by the at least one processor, periodically for each resource platform of the plurality of resource platforms, according to at least one refresh period, at least one subsequent abstracted query configured to synchronize the plurality of resource objects with the plurality of resource platforms; generating, by the at least one processor, based on the at least one refresh period, at least one subsequent respective normalized application programming interface call to each respective resource platform by modifying the at least one subsequent abstracted query for each respective resource platform of the plurality of resource platforms based on each respective application programming interface of the plurality of application programming interfaces; and storing, by the at least one processor, responsive to the at least one subsequent respective normalized application programming interface call to each of the plurality of resource platforms, in the resource cache, a plurality of refreshed resource objects for each resource platform, wherein the plurality of refreshed resource objects includes an up-to-date record of each resource of the plurality of resources managed by the plurality of resource platforms, including: an updated availability property indicating a current availability of the respective resource, and an updated capability property indicating a current capability of the respective resource.

In some aspects, the techniques described herein relate to a method, wherein the at least one refresh period includes one day.

In some aspects, the techniques described herein relate to a method, wherein the plurality of refreshed resource objects includes the up-to-date record for changed resources of the plurality of resources.

In some aspects, the techniques described herein relate to a method, wherein the plurality of refreshed resource objects includes the up-to-date record for all the plurality of resources.

In some aspects, the techniques described herein relate to a method, wherein the plurality of resource platforms includes a plurality of electronic health record (EHR) integrations.

In some aspects, the techniques described herein relate to a method, wherein the plurality of resources includes a plurality of healthcare providers.

BRIEF DESCRIPTION OF THE DRAWINGS

Various embodiments of the present disclosure can be further explained with reference to the attached drawings, wherein like structures are referred to by like numerals throughout the several views. The drawings shown are not necessarily to scale, with emphasis instead generally being placed upon illustrating the principles of the present disclosure. Therefore, specific structural and functional details disclosed herein are not to be interpreted as limiting, but merely as a representative basis for teaching one skilled in the art to variously employ one or more illustrative embodiments.

DETAILED DESCRIPTION

Figure 1:
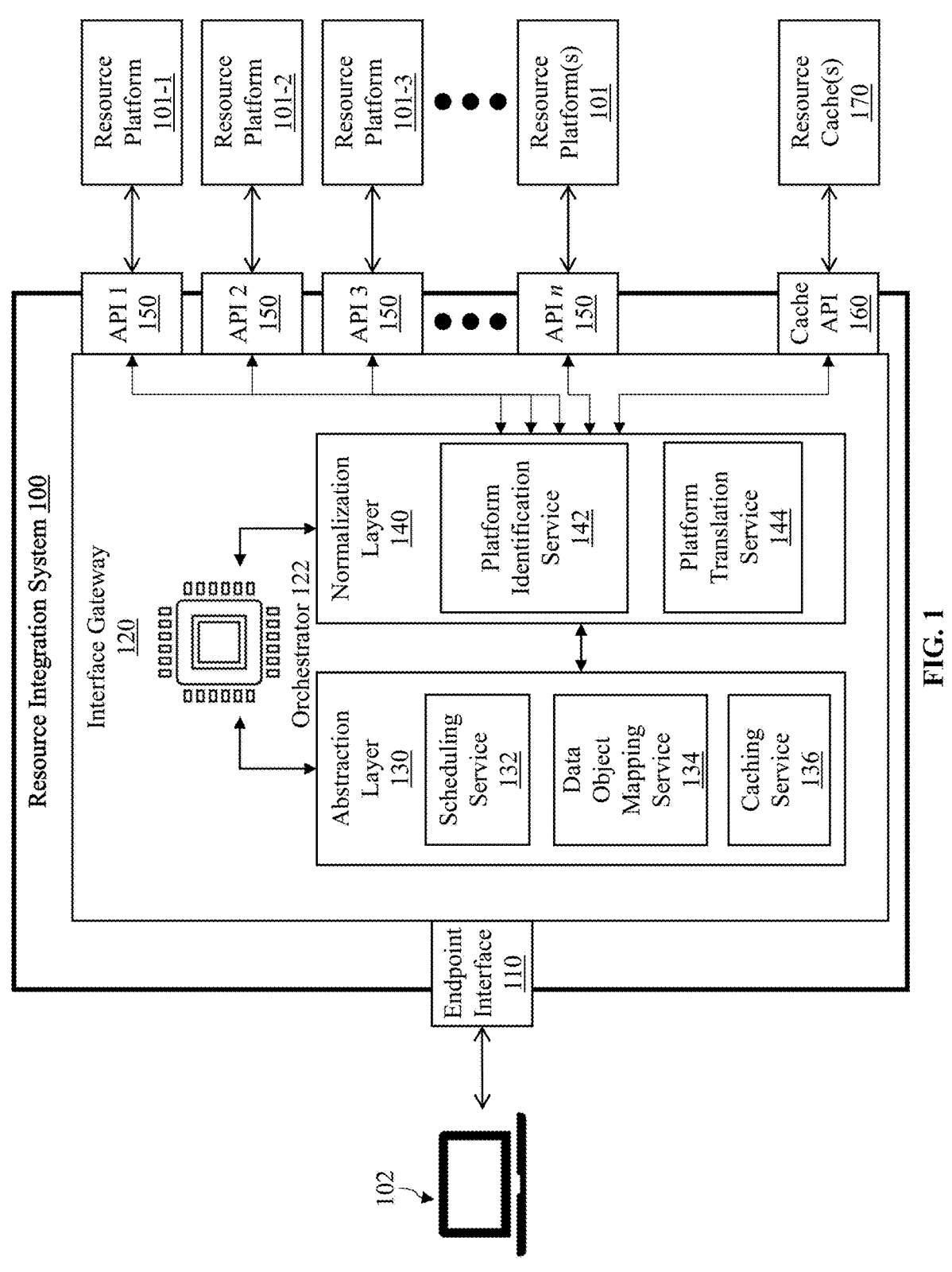
FIG. 1 depicts a resource integration system in accordance with some embodiments of the present disclosure.

Various detailed embodiments of the present disclosure, taken in conjunction with the accompanying FIGs., are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the terms "and" and "or" may be used interchangeably to refer to a set of items in both the conjunctive and disjunctive to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

FIGS. 1 through 12 illustrate systems and methods of real-time resource platform. The following embodiments provide technical solutions and technical improvements that overcome technical problems, drawbacks and/or deficiencies in the technical fields involving compatibility with multiple third-party APIs for unified access to resources from multiple platforms, and efficient synchronization with multiple platforms. As explained in more detail, below, technical solutions and technical improvements herein include aspects of improved API call normalization for scalable and flexible API calls that integrate with various platforms, proactive and/or real-time caching of the various resources, and efficient orchestration of client queries, resource API calls and cache querying to answer the client queries most efficiently and quickly with up-to-date and synchronized resources In some embodiments, API calls can be more efficiently and implemented at scale using a normalization layer and/or an abstraction layer for communicating with various platforms associated with various resources. In some embodiments, normalization/abstraction layer(s) generates an abstracted query for related resources managed by each resource platform. The query may be normalized to generate custom API calls specific to each resource for querying each platform for the resources. As is described in more detail below, a dynamically updated mapping and abstraction service may be leveraged to automatically create each custom API call from the custom API call. Accordingly, one query can be used to structure multiple API calls, thus requiring fewer user inputs while automatically calling each platform applicable to the abstracted query.

In some embodiments, to more efficiently deliver and onboard the resources from the various platforms, the resources may be mapped from any format from any platform into object fields associated with characteristics of each resource. By having the unstructured response from each platform stored in a resource cache, the system can then handle requests from users to reserve and/or utilize resources of any platform.

In some embodiments, resources from the various platforms can be more efficiently retrieved in response to the abstracted query by onboarding platform-specific queries in response to the API calls. In some embodiments, the platforms can respond with updates about the resources which may be stored in the resource cache for on-demand access in response to future queries without calling the various platforms, thus reducing network activity and processing resources.

Based on such technical features, further technical benefits become available to users and operators of these systems and methods. Moreover, various practical applications of the disclosed technology are also described, which provide further practical benefits to users and operators that are also new and useful improvements in the art.

Figure 2:
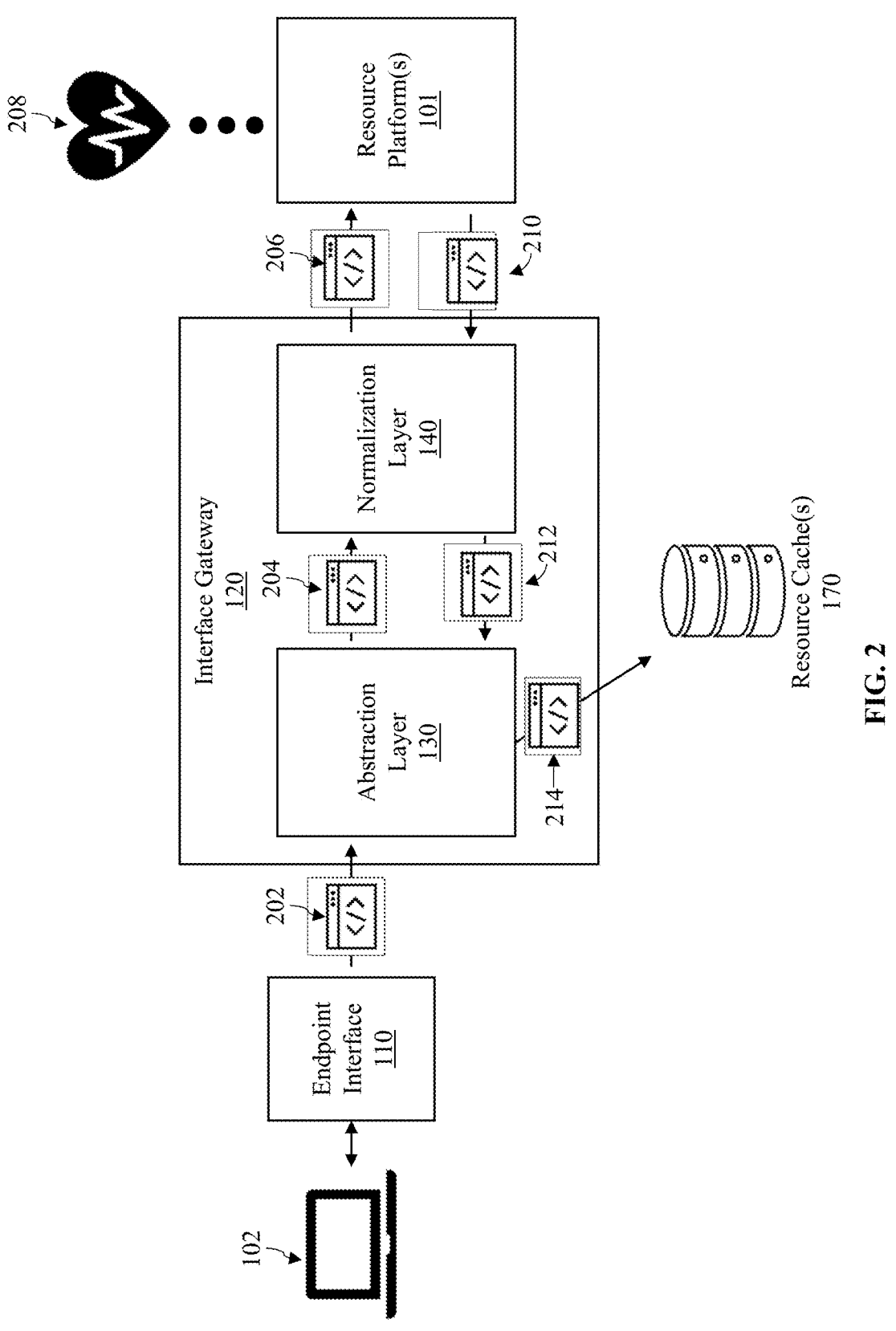
FIG. 2 depicts an API gateway of a resource integration system in accordance with some embodiments of the present disclosure.
Figure 3:
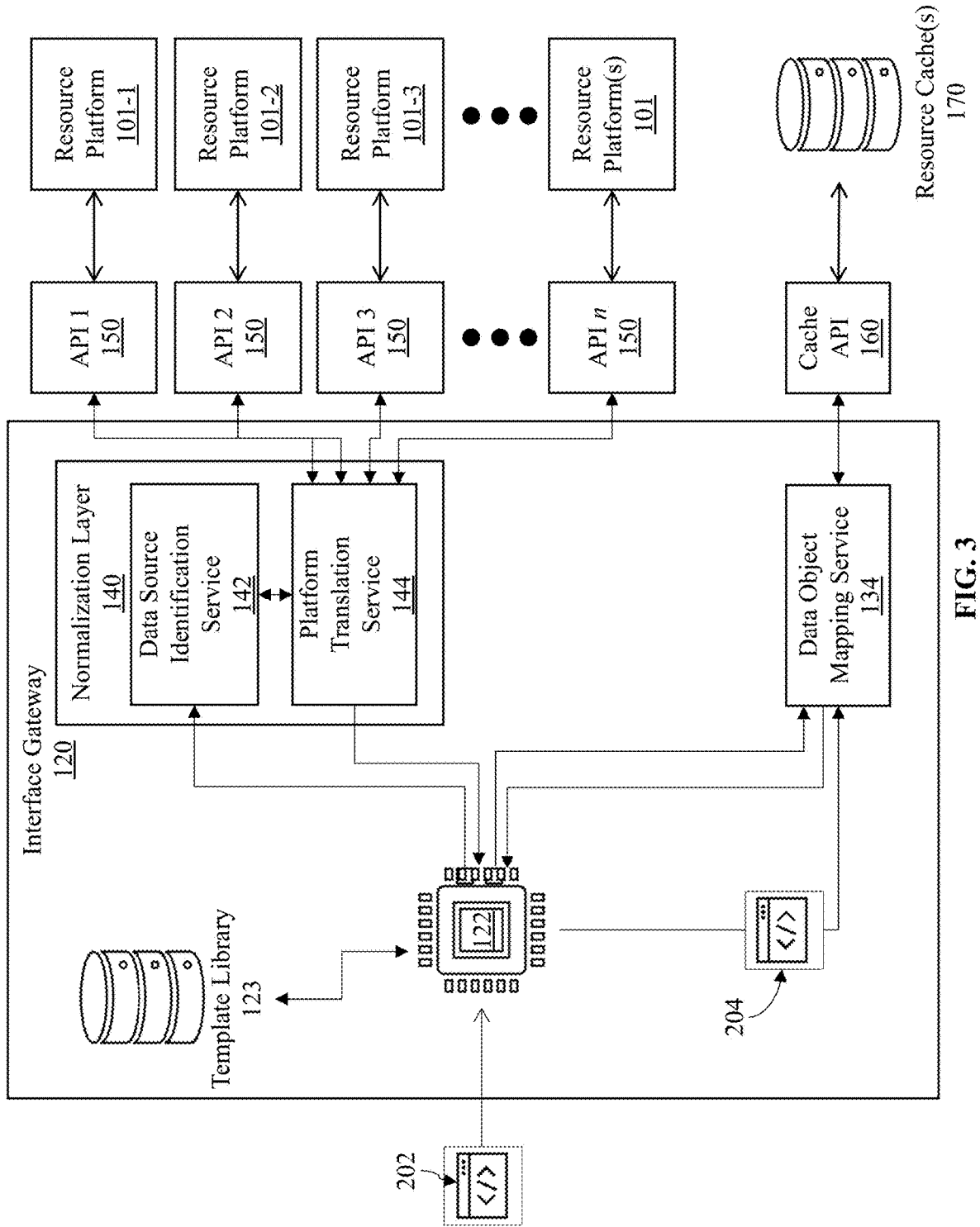
FIG. 3 depicts an API gateway of a resource integration system in accordance with some embodiments of the present disclosure.

Referring generally to FIGS. 1-3, a resource integration system 100 is illustrated in accordance with some embodiments of the present disclosure. In some embodiments, a resource integration system 100 may include an interface gateway 120 with an abstraction layer 130 and a normalization layer 140 for communicating with various resource platforms 101 that manage resources 208. The resources may be electronic representations of devices, machines, providers, and/or equipment. In some embodiments, the resources 208 may describe devices, machines, equipment, and/or healthcare providers.

The resource integration system 100 may manage resource objects 214 to standardize the representation of the resources 208. The resource integration system 100 may generate an abstract query 204 via the cache API 160 for properties (e.g., availability) of resource objects 214 in the resource cache 170. To obtain attributes about resources 208 from the platforms 101, the resource integration system 100 may normalize the abstract query 204 to generate a customized application programming interface call 206 (e.g., custom API call) for querying each platform 101 for attributes about the resources 208. For example, the resource integration system 100 may have the extensiveness and comprehensiveness to generate 3 API calls.

In response to the customized application programming interface call 206, the resource platforms 101 may respond with unstructured responses 210 that include the attributes about the resources 208. The resource integration system 100 may generate a normalized response 212 from the unstructured response 210. The resource integration system 100 may generate a resource object 214 from the normalized responses 212 for storage in resource cache 170. The resource integration system 100 may map the normalized responses 212 received in any format from any platform 101 into the resource object 214 fields of resource, availability, and capability. For example, the resource object 214 may identify the resource 208 and its availability (e.g., next Friday at 9 am) and capability (e.g., whether the device is for child or adult).

By having resource objects 214 associated with each platform 101 stored in the resource cache 170, the resource integration system 100 may handle resource requests 202 from the client devices 102 to utilize (e.g., schedule appointments) of the resources 208 of any platform 101. The resource integration system 100 may schedule the usage of resources 208 managed by any platform 101 to satisfy the resource requests 202. By determining a common denominator (e.g., abstracted query 204) of attributes that can be requested from the disparate platforms and generate the API calls (e.g., customized application programming interface call 206) that are dynamically adapted to any format that the resource platforms 101 may have based on the common denominator, the resource integration system 100 can obtain enriched attributes about the resources 208 from any of the resource platforms 101 in response to any resource request 202 from the client devices 102.

In some embodiments, the resource integration system 100 may include an interface gateway 120 configured to interface with at least one client device 102 and a plurality of resource platforms 101. In some embodiments, the plurality of resource platforms 101 may be a plurality of electronic health record (EHR) integrations. In some embodiments, the resource integration system 100 may implement computer engines for interacting with the client device 102 via the endpoint interface 110 to obtain resource requests 202 to construct an abstracted query 204. In some embodiments, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

The interface gateway 120 may include a resource orchestrator 122 that includes at least one processor in communication with at least one non-transitory computer-readable medium having software instructions stored thereon. In some embodiments, the resource orchestrator 122 may include hardware components such as a processor, which may include local or remote processing components. In some embodiments, the processor may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processor may include data-processing capacity provided by the microprocessor. In some embodiments, the microprocessor may include memory, processing, interface resources, controllers, and counters. In some embodiments, the microprocessor may also include one or more programs stored in memory.

The interface gateway 120 may include one or more data stores, including a directory and/or template library, such as one or more local and/or remote data storage solutions such as, e.g., local hard-drive, solid-state drive, flash drive, database or other local data storage solutions or any combination thereof, and/or remote data storage solutions such as a server, mainframe, database or cloud services, distributed database or other suitable data storage solutions or any combination thereof. In some embodiments, the data store(s) may include, e.g., a suitable non-transient computer readable medium such as, e.g., random access memory (RAM), read only memory (ROM), one or more buffers and/or caches, among other memory devices or any combination thereof.

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, the endpoint interface 110 may utilize one or more software computing interface technologies, such as, e.g., Common Object Request Broker Architecture (CORBA), an application programming interface (API) and/or application binary interface (ABI), among others or any combination thereof. In some embodiments, an API and/or ABI defines the kinds of calls or requests that can be made, how to make the calls, the data formats that should be used, the conventions to follow, among other requirements and constraints. An "application programming interface" or "API" can be entirely custom, specific to a component, or designed based on an industry-standard to ensure interoperability to enable modular programming through information hiding, allowing users to use the interface independently of the implementation. In some embodiments, CORBA may normalize the method-call semantics between application objects residing either in the same address-space (application) or in remote address-spaces (same host, or remote host on a network). In some embodiments, one or more interfaces may utilize one or more hardware computing interface technologies, such as, e.g., Universal Serial Bus (USB), IEEE 1394 (FireWire), Ethernet, Thunderbolt™, Serial ATA (SATA) (including eSATA, SATAe, SATAp, etc.), among others or any suitable combination thereof.

In some embodiments, the client device 102 may include one or more computing devices, including, e.g., at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth. For example, as shown in FIG. 11, the client device 102 may be a mobile device 1104, a computer 1106, administrator device 1110, and/or a provider portal 1114.

In some embodiments, the client device 102 may communicate with the resource integration system 100 via the endpoint interface 110 to access data provided by one or more of the resource platforms 1, 2, 3 through n. In some embodiments, there may be a front-end client for each user type associated with the resource integration system 100. For example, a customer accessing data for personal user, a business accessing data for company, enterprise, employee, etc. use, an administrator accessing the resource integration system 100 for administration purposes, a platform owner accessing the resource platform(s) 1, 2, 3 through n, e.g., for configuring and/or development tasks, among other user types or any combination thereof.

Figure 11:
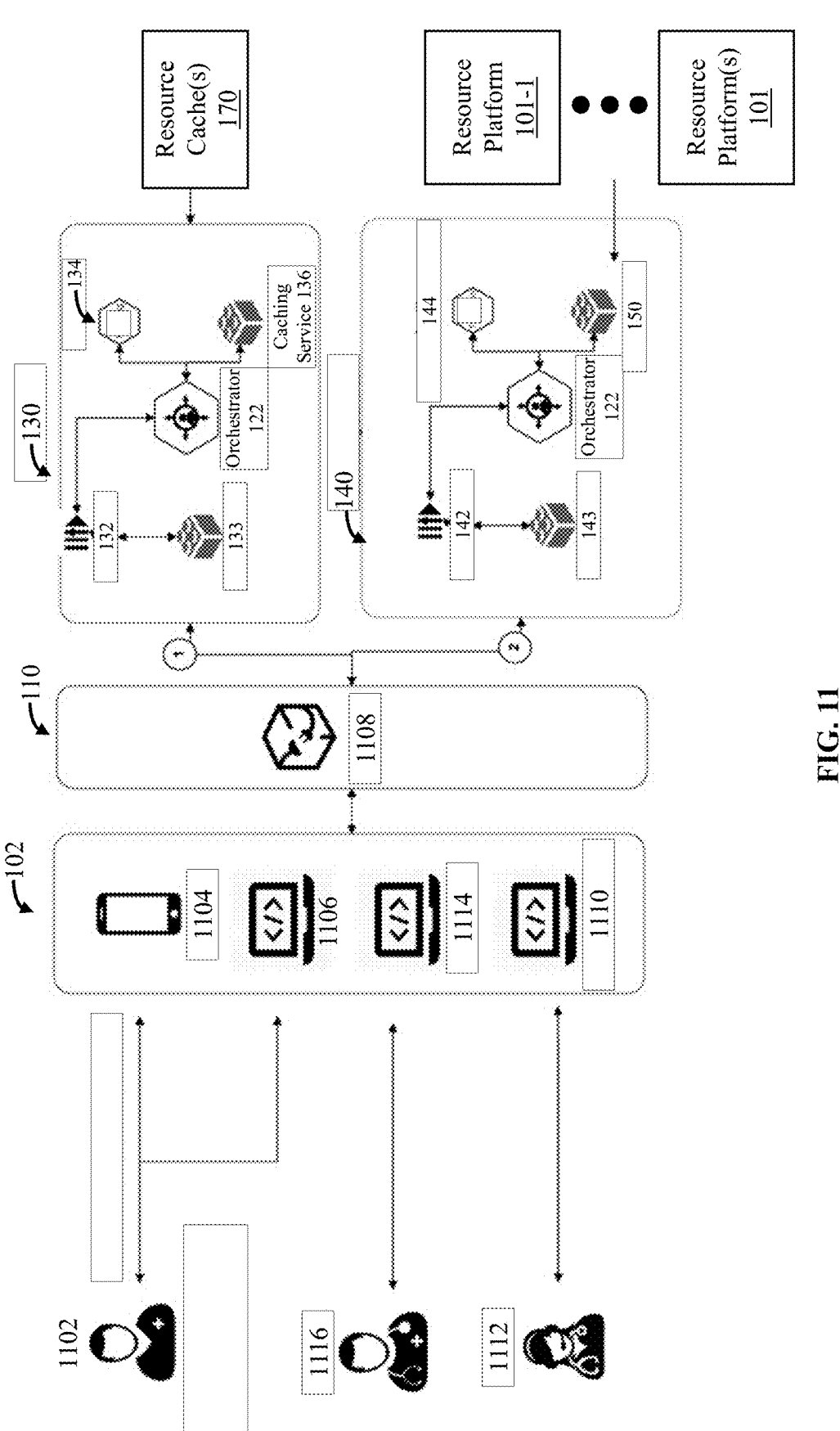
FIG. 11 depicts an example resource integration system for electronic health records (EHR) platform integration in accordance with some embodiments of the present disclosure.

For example, as shown in FIG. 11, the endpoint interface 110 may include an API gateway 1108 for facilitating communications between the mobile device 1104 or the computer 1106 of the user 1102 and the resource integration system 100. In another example, as shown in FIG. 11, the endpoint interface 110 may include the API gateway 1108 that may facilitate communications between a provider portal 1114 of a provider 1116 (e.g., physician) and the resource integration system 100. In another example, as shown in FIG. 11, the endpoint interface 110 may include the API gateway 1108 that may facilitate communications between an administrator device 1110 and the resource integration system 100.

In some embodiments, the resource integration system 100 may receive attributes about the resources 208 from the administrator device 1110. For example, the resource integration system 100 may receive an import of the attributes of the resources 208 from which the resource integration system 100 may initialize or generate the resource objects 214 for storage in the resource cache 170. As further described below, the resource integration system 100 can communicate with the resource platforms 101 to update the existing resource objects 214 and add new resource objects 214.

Figure 9:
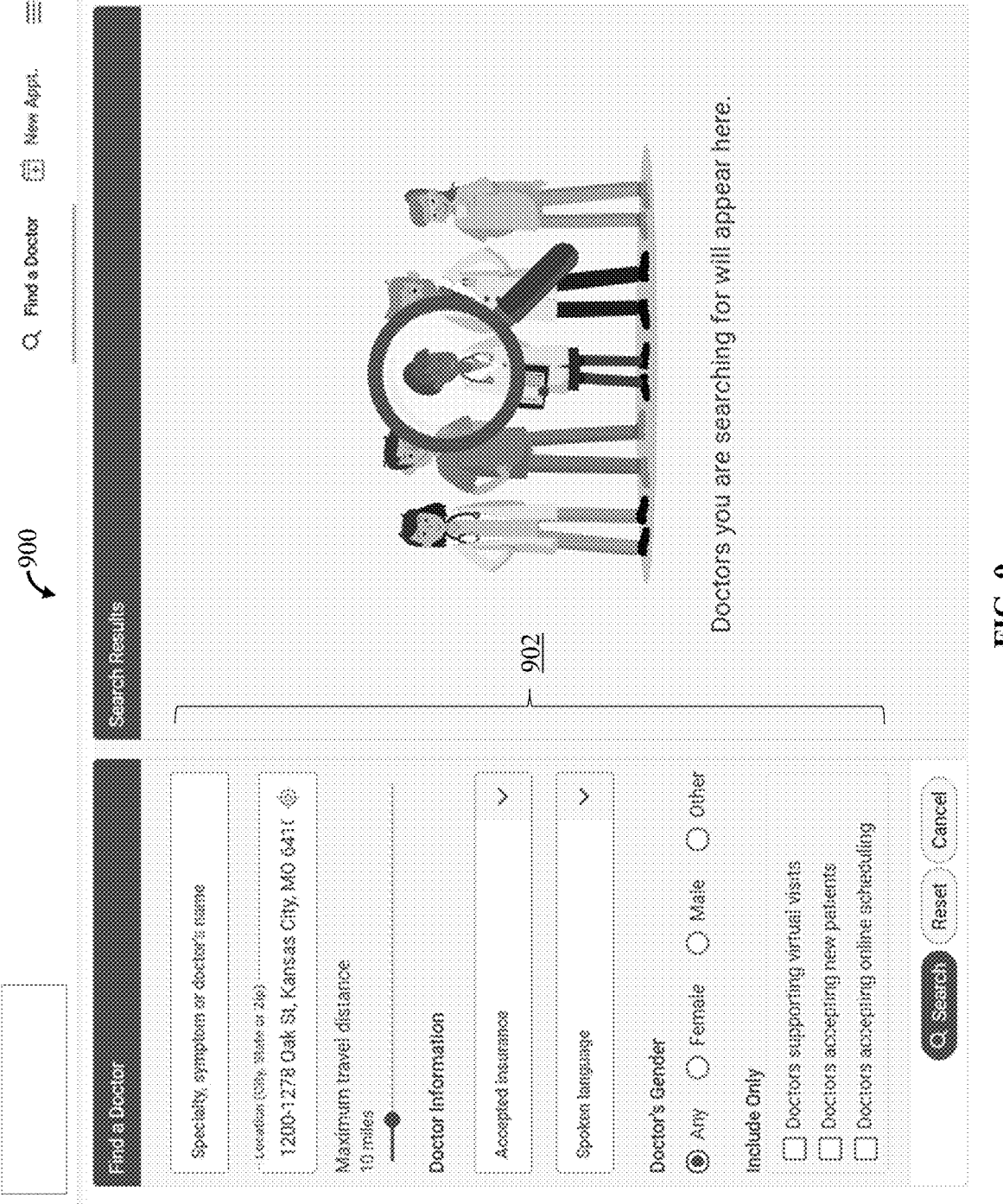
FIG. 9 depicts an example client interface for submitting a resource request including a healthcare provider resource in accordance with some embodiments of the present disclosure.

Now referring to FIG. 9, in some embodiments, the client device 102 displays interfaces 900 for obtaining resource requests 202. For example, as shown in FIG. 11, the user 1102 may be a patient that interacts with the interfaces 900. In some embodiments, the endpoint interface 110 may enable access to the system 100 via one or more front-end client interfaces 900. For example, the front-end client interfaces 900 may include, e.g., a webpage, a native application on one or more operating systems, a message adapter, a software development kit (SDK), a terminal/thin client, or other front-end client or any combination thereof.

Figure 12:
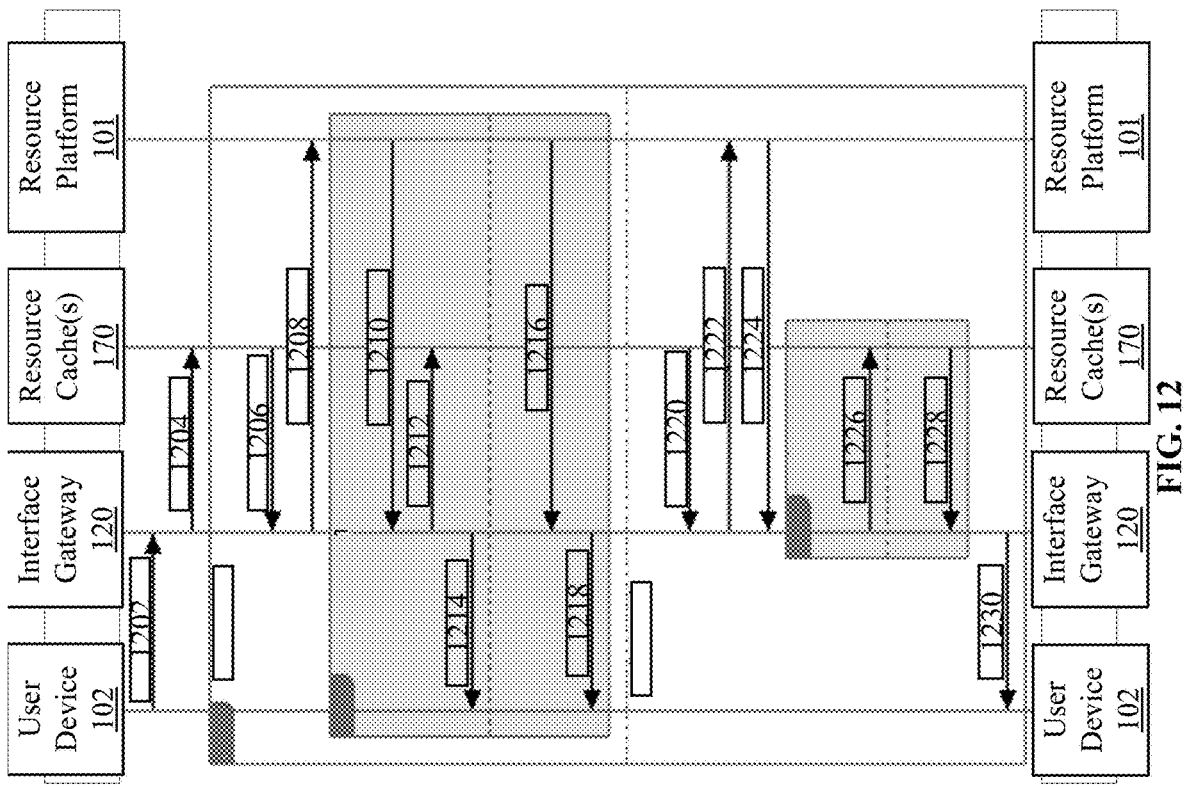
FIG. 12 depicts an example messaging flow for based on the object mapping for accessing provider resource data in accordance with some embodiments of the present disclosure.

For example, as shown in FIG. 12, in flow 1202, the interface gateway 120 may receive a resource request 202 from the client device 102. In some embodiments, when attempting to access data provided by one or more of the resource platforms 1, 2, 3 through n 101, the user 1102 may communicate from the client device 102 with the resource integration system 100 via an endpoint interface 110 to define a resource request 202. For example, the client device 102 may receive interactions from the user 1102 via the interface 900 for submitting a resource request 202 including a healthcare provider resource.

In some embodiments, the resource requests 202 can include a resource request attribute defining at least one requested capability of the resource 208. For example, the interfaces 900 may include user interface elements 902 that are user selectable and/or user input fields for defining resource request attributes of the resource request 202. In some embodiments, the resource request 202 includes at least one user attribute associated with the user 1102 of the client device 102. For example, the user attribute can be an identifier that identifies the user 1102. The resource requests 202 may be transmitted from the client device 102 to the interface gateway 120 via the endpoint interface 110. The interface gateway 120 may receive the resource requests 202. In some embodiments, the interface gateway 120 receives from the at least one client device 102, the resource request 202 representing at least one request for at least one resource of the plurality of resources.

In some embodiments, to dynamically generate prompts in the interface 900 to obtain the resource requests 202, the resource integration system 100 may include computer engines including, e.g., a questionnaire service. In some embodiments, the questionnaire service may include dedicated and/or shared software components, hardware components, or a combination thereof. For example, the questionnaire service may include a dedicated processor and storage. However, in some embodiments, the questionnaire service may share hardware resources, including the processor of the resource orchestrator 122 of the interface gateway 120.

The interface gateway 120 may include an abstraction layer 130 and a normalization layer 140 to provide improved integration of data from resource platforms 1, 2, 3 through n 101. In some embodiments, the interface gateway 120 may be an API management tool that sits between the client device 102 and one or more backend services, including resource platforms 101. In some embodiments, the interface gateway 120 may include one or more software-based services to provide software security, data communication/ message routing, rate limiting, user authentication, error detection, system monitoring and/or analytics, as well as API orchestration and management, among other functionalities or any combination thereof. For example, authentication with the platforms 101 may be based on API Keys, Open Authorization (OAUTH), and/or Fast Healthcare Interoperability Resources (FIHR).

In some embodiments, the abstraction layer 130 and the normalization layer 140 may enable access to APIs 1, 2, 3 through n 150 associated with the resource platforms 1, 2, 3 through n 101 using common format ("abstracted") API calls or queries (e.g., abstracted query 204). For example, as shown in FIG. 12, in flow 1204, the interface gateway 120 may transmit an abstract query 204 to the resource cache 170 to identify resource objects 214 to satisfy the resource request 202. In some embodiments, the abstraction layer 130 may map resource requests 202 to a common format ("abstracted") query or API call that includes data common to each API 1, 2, 3 through n 150. In some embodiments, the abstraction layer 130 may generate an abstracted query 204 about the plurality of resources 208 managed by the plurality of resource platforms 101.

In some embodiments, the abstraction layer 130 may use attributes provided by the resource request 202 to structure the abstracted query 204. In some embodiments, the abstraction layer 130 may generate the abstracted query 204 for each respective resource of the plurality of resources 208. In some embodiments, the abstraction layer 130 may generate the abstracted query 204 for an availability of each respective resource of the plurality of resources 208. In some embodiments, the abstraction layer 130 may generate the abstracted query 204 for a capability of each respective resource of the plurality of resources 208.

In some embodiments, the abstraction layer 130 may generate the abstracted query 204 to query the cache 170 for the resources 208 represented by the resource objects 214. For example, as shown in FIG. 12, in flow 1206, the interface gateway 120 may determine that the cache 170 does not have any resource objects 214 for resources 208 to satisfy the resource request 202. Conversely, for example, as shown in FIG. 12, in flow 1220, the interface gateway 120 may determine that the cache 170 has resource objects 214 for resources 208 to satisfy the resource request 202. If the cache 170 has the resource objects 214 that are available, the interface gateway 120 may transmit the resource objects 214 for display as shown in flow 1230.

For example, in some embodiments, the interface gateway 120 may receive the resource request 202 from the client device 102 of the user. The resource request 202 may include a resource attribute defining a requested resource 208. The abstraction layer 130 may query, using the at least one resource attribute, the resource cache 170 to identify at least one resource object 214 having at least one capability matching the at least one resource attribute in response to the resource request 202.

In some embodiments, the abstraction layer 130 may query, using a plurality of resource attributes, the resource cache 170 to identify at least one resource object 214 having at least one capability matching the at least one resource attribute in response to the resource request 202, including multiple resource attributes, one or more resource attributes according to multiple properties, compound resource attributes (e.g., a resource attribute formed from multiple sub-attributes) or any other combination of resource attributes and/or properties thereof. For example, the abstraction layer 130 may query numerous attributes to identify one or more resource objects 214 that have matching properties. In some embodiments, the abstraction layer 130 may determine that the resource object 214 is not present in the resource cache 170.

In some embodiments, if the resource objects 214 are unavailable in the resource cache 170, the abstraction layer 130 may transmit the abstracted query 204 to the normalization layer 140. For example, as shown in FIG. 12, in flow 1208, the interface gateway 120 may transmit the API call 206 to the platforms 101 associated with the resources 208. The normalization layer 140 may communicate, based on the at least one resource object 214 not being present in the resource cache 170, the resource request 202 to a resource platform 101. The normalization layer 140 may receive, from the platform 101, at least one resource assignment reserving at least one resource 208 for the user. For example, if the resource object 214 describing the resource 208 is not in the cache, the normalization layer 140 may return, from the platform 101, the newest value associated with the resource 208.

In some embodiments, the platform identification service 142 of the normalization layer 140 of the interface gateway 120 may generate a respective customized application programming interface call 206 to each respective resource platform 101 by modifying the abstracted query 204 for each respective resource platform 101 of the plurality of resource platforms 101. The customized application programming interface call 206 may be formatted to be compatible with the platforms 101 so that the platforms 101 may respond with attributes about the resource 208.

The following tables depict examples of the customized application programming interface calls 206 in the resource integration system 100 for EHR platform integration.

TABLE 1

| Authentication | |
| --- | --- |
| Post | /API/Authentication/token |

In some embodiments, as shown in Table 1, the interface gateway 120 may generate the customized application programming interface calls 206 to transmit (e.g., post) an authentication token to the platform 101. For example, the authentication token may be a security key that enables the interface gateway 120 to access the platform 101.

TABLE 2

| EHR/Admin | | |
| --- | --- | --- |
| Get | /API/EHR/Admin/Practice | Return list of Practice |
| Get | /API/EHR/Admin/Practice | Return Department list |

In some embodiments, as shown in Table 2, the interface gateway 120 may generate the customized application programming interface calls 206 to request (e.g., get) attributes about the resources 208 managed by the platforms 101 (e.g., EHR). For example, the customized application programming interface calls 206 may request a list of practices managed by the platforms 101. In another example, the customized application programming interface calls 206 may request a list of departments managed by the platforms 101. In some implementations, the interface gateway 120 may generate the customized application programming interface calls 206 in response to a resource request 202 received from the administrator device 1110 of the administrator 1112. For example, the administrator 1112 may want to access the resources 208 to see what is available for the user 1102.

TABLE 3

| | | EHR/Patient |
|---|---|---|
| Get | /API/EHR/Patient | Returns patient information from her |
| Put | /API/EHR/Patient | Update an existing patient in EHR platform |
| Post | /API/EHR/Patient | Create a new patient in EHR platform |
| Get | /API/EHR/Patient/Find | Find Patient based on DOB and ZIP |

In some embodiments, as shown in Table 3, the interface gateway 120 may generate the customized application programming interface calls 206 to request (e.g., get) attributes about the user 1102 (e.g., patient) from the platforms 101 (e.g., EHR). For example, the customized application programming interface calls 206 may request patient information from the platforms 101. In another example, the customized application programming interface calls 206 may request attributes of the user 1102 based on their date of birth (DOB) and zip code. In some embodiments, the interface gateway 120 may generate the customized application programming interface calls 206 to modify (e.g., put) attributes about the user 1102 (e.g., patient) stored by the platforms 101. For example, the customized application programming interface calls 206 may update an existing patient in the platforms 101. In some embodiments, the interface gateway 120 may generate the customized application programming interface calls 206 to transmit (e.g., post) attributes about the user 1102 (e.g., patient) that is new to the platforms 101. For example, the customized application programming interface calls 206 may create a new patient in the platforms 101. In some implementations, the interface gateway 120 may generate the customized application programming interface calls 206 in response to a resource request 202 received by the interface gateway 120 from the mobile device 1104 or the computer 1106 of the user 1102. For example, the user 1102 may want to access the resources 208 associated with their own attributes such as demographic information.

TABLE 4

| | | EHR/Provider |
|---|---|---|
| Get | /API/EHR/Provider | Returns provider information |
| Get | /API/EHR/Provider | Return the list of providers |

In some embodiments, as shown in Table 4, the interface gateway 120 may generate the customized application programming interface calls 206 to request (e.g., get) properties about the resources 208 (e.g., devices of a provider) from the platforms 101 (e.g., EHR). For example, the customized application programming interface calls 206 may request patient information from the platforms 101. In another example, the customized application programming interface calls 206 may request attributes of the user 1102 based on their date of birth and zip code. In some implementations, the interface gateway 120 may generate the customized application programming interface calls 206 in response to a resource request 202 received by the interface gateway 120 from the provider portal 1114 of the provider 1116. For example, the provider 1116 may want to access the resources 208 to see attributes of resources 208 associated with the provider 1116.

In some embodiments, the platform identification service 142 may determine a set of additional application programming interface fields in each respective customized application programming interface call 206. For example, the additional application programming interface fields may be for communicating with a particular platform 101. The set of additional application programming interface fields may be in addition to a set of abstracted query fields of the abstracted query 204. The set of abstracted query fields may define each respective resource of the plurality of resources 208. Examples of fields may also include Date of Birth (DOB), Department, Email, Guarantor Email, SSN, Home Phone, Mobile Phone, Work Phone, and/or ZIP Code.

In some embodiments, the object mapping service 134 may determine a set of additional application programming interface data for each respective customized application programming interface call 206 to populate the set of additional application programming interface fields based at least in part on the plurality of resource objects 214 associated with the abstracted query 204. In some embodiments, the resource integration system 100 may generate the respective customized application programming interface call 206 to each respective resource platform 101 by modifying the abstracted query 204 for each respective resource platform of the plurality of resource platforms 101 to include the set of additional application programming interface fields comprising the set of additional application programming interface data of each respective customized application programming interface call 206.

In some embodiments, the platform identification service 142 may generate the customized application programming interface call 206 based on the application programming interfaces (APIs) 150. In some implementations, as shown in FIG. 11, the platform identification service 142 may use API generation rules 143 (e.g., Representational state transfer (REST) API) to generate the customized application programming interface call 206 with the platforms 101. In some embodiments, each of API 1 150, API 2 150, API 3 150 through API n 101 may include one or more APIs associated with a corresponding resource platform 1 101, resource platform 2 101, resource platform 3 101 through resource platform n 101. For example, the API(s) of each API 1, 2, 3 through n 150 may include, e.g., any definition of the kinds of calls or requests that can be made, how to make the calls, the data formats that should be used, the conventions to follow, among other requirements and constraints.

In some embodiments, the API(s) of each API 1, 2, 3 through n 150 may be entirely custom, specific to a component, or designed based on an industry-standard to ensure interoperability to enable modular programming through information hiding, allowing users to use the interface 150 independently of the implementation. In some embodiments, one or more other software and/or hardware interfaces may be employed in addition to or instead of one or more of API 1, 2, 3 through n 150. Additionally, or alternatively, the APIs 150 include support for a procedure call (RPC), which can be when the APIs 150 cause a procedure (e.g., subroutine) to execute in a different address space (e.g., resource platforms 101), such as to facilitate the customized application programming interface call 206 to the resource platform 101 or receive the unstructured responses 210 from the platforms 101. Examples of API formats/structures may include, e.g., representation state transfer (REST) (e.g., Fast Healthcare Interoperability Resources (FHIR) or other RESTful protocol or combination thereof), Simple Object Access Protocol (SOAP), server application programming interface (SAPI), or other API technology or any combination thereof. In some embodiments, the APIs 1, 2, 3 through n 150 may have various structures and/or data field requirements. For example, based on each client 102, the API 150 may be customized with authentication requirements, permissions, and/or API functions associated with each user type.

In some embodiments, the platform identification service 142 may identify or select a plurality of APIs 150 maintained by the normalization layer 140 for querying the plurality of resource platforms 101 about the plurality of resources 208 managed by the plurality of resource platforms 101. For example, as shown in FIG. 11, the APIs 150 may be included in the normalization layer 140 for facilitating communications between the integration system 100 and the platforms 101. In some embodiments, the resource integration system 100 may identify three APIs. For example, one API for each platform 101.

In some embodiments, the interface gateway 120 may catalog the structures and/or requirements of each API 1, 2, 3 through n 150 integrated on the resource integration system 100, and the abstraction layer 130 use the catalog of structures and/or requirements to determine a common denominator of information that is common to all APIs. For example, where each resource platform 1, 2, 3 through n 101 provide data for a particular context (e.g., merchant data, healthcare provider data, health records, multimedia, etc.), each resource platform 1, 2, 3 through n 101 may employ one or more respective APIs 1, 2, 3 through n 150 to define requested data.

In some embodiments, the plurality of APIs 150 may be defined by a plurality of resource selection questionnaire templates specific to each respective resource platform of the plurality of resource platforms 101. The resource integration system 100 may store the questionnaire templates in a template library 123. In some embodiments, the platform identification service 142 dynamically returns questionnaires based on the template questionnaires in the template library 123. The template questionnaires may include resource platform-specific templates for structuring the customized application programming interface call 206 based on the abstract queries 204.

The platform identification service 142 may adapt the abstracted query 204 to a resource platform 101 having multiple APIs associated therewith. For example, the normalization layer 140 may adapt the abstracted query 204 for each resource platform 101 depending on its respective API 150. Where a particular one or more of API 1 140, API 2 140, API 3 140 through API n 101 include multiple APIs for a corresponding resource platform 1 101, resource platform 2 101, resource platform 3 101 through resource platform n 101, the normalization layer 140 may translate the abstracted query 204 into a customized application programming interface call 206 that is particular for one or more of the APIs 150.

In some embodiments, the platform identification service 142 may generate a respective customized application programming interface call 206 to each respective resource platform 101 by modifying the abstracted query 204 for each respective resource platform 101 of the plurality of resource platforms 101 based on each respective application programming interface of the plurality of application programming interfaces 150. For example, the platform identification service 142 may translate the abstracted query 204 into customized application programming interface call 206 that are resource platform-specific API calls associated with each API 1, 2, 3 through n 150. In some embodiments, the platform identification service 142 may generate the customized application programming interface call 206 for a particular resource platform 101 based on the questionnaire templates associated with the APIs 150 associated with that resource platform 101.

In some embodiments, the platform translation service 144 of the normalization layer 140 may receive an unstructured response 210 from the platforms 101. For example, as shown in FIG. 11, the interface gateway 120 may communicate via a provider portal 1114 with a provider 1116 (e.g., physician) that provides attributes about the resources 208. In some embodiments, the platform translation service 144 may receive the unstructured response 210 from each of the plurality of resource platforms 101 via the APIs 150 in response to the customized application programming interface call 206.

In some embodiments, as shown in FIG. 12, in flow 1210, the interface gateway 120 may receive the unstructured response 210 from the platform 101 with attributes about the resource 208. In some embodiments, the platform translation service 144 may receive the unstructured response 210 responsive to the respective customized application programming interface call 206 to each of the plurality of resource platforms 101.

In some embodiments, the unstructured response 210 may include platform-specific formatting. In some embodiments, the unstructured response 210 may include attributes indicative of the respective resource 208. For example, the unstructured response 210 may include a list of practices from the platform 101. In another example, the unstructured response 210 may include a list of departments from the platform 101 In some embodiments, the unstructured response 210 may be indicative of the availability of the respective resource 208. In some embodiments, the unstructured response 210 may be indicative of the capability of the respective resource 208. In another example, the unstructured response 210 may include patient information from the platform 101. In another example, the unstructured response 210 may include a patient based on their ZIP code and date of birth. In another example, the unstructured response 210 may include provider information from the platform 101. In another example, the unstructured response 210 may include a list of providers from the list of providers in the platform 101.

In some embodiments, the interface gateway 120 may identify that the unstructured response 210 indicates that there aren't any resources 208 of the platforms 101 that can satisfy the resource request 202. For example, as shown in FIG. 12, in flow 1216, the interface gateway 120 may receive an unstructured response 210 from the platform 101 that indicates that there are no resources 208 that can satisfy the resource request 202. For example, the unstructured response 210 from the platform 101 may indicate that the resource 208 is unavailable or not found.

In some embodiments, the platform translation service 144 of the normalization layer 140 may generate a normalized response 212 from the unstructured response 210. The platform translation service 144 may map the normalized responses 212 received in any format from any platform 101 into the normalized response 212 fields of resource, availability, and capability. For example, the normalized response 212 may identify the resource 208 and its availability (e.g., next Friday at 9 am) and capability (e.g., whether the device is for child or adult). In another example, the normalized response 212 may include a list of practices from the platform 101. In another example, the normalized response 212 may include a list of departments from the platform 101. In another example, the normalized response 212 may include patient information from the platform 101. In another example, the normalized response 212 may include a patient based on their ZIP code and date of birth. In another example, the normalized response 212 may include provider information from the platform 101. In another example, the normalized response 212 may include a list of providers from the list of providers in the platform 101.

In some embodiments, the abstraction layer 130 may include an object mapping service 134 that may map the normalized response 212 to resource objects 214. The object mapping service 134 may map the attributes in the normalized responses 212 from the resource platforms 101 to the resource objects 214 by linking the attributes to properties and values of the resource objects 214. Each of the resource objects 214 may include one or more properties 216 with one or more corresponding values 218 to describe the resources 208. The resources 208 may be electronic representations of devices, machines, providers, and/or equipment. In some embodiments, the resources 208 may describe devices, machines, equipment, and/or healthcare providers. In some embodiments, the resource objects 214 may be standardized representations of the resources 208. For example, the resource objects 214 may be electronic representations of devices, machines, providers, and/or equipment. In some embodiments, the resource objects 214 may describe devices, machines, equipment, and/or healthcare providers.

Figure 10:
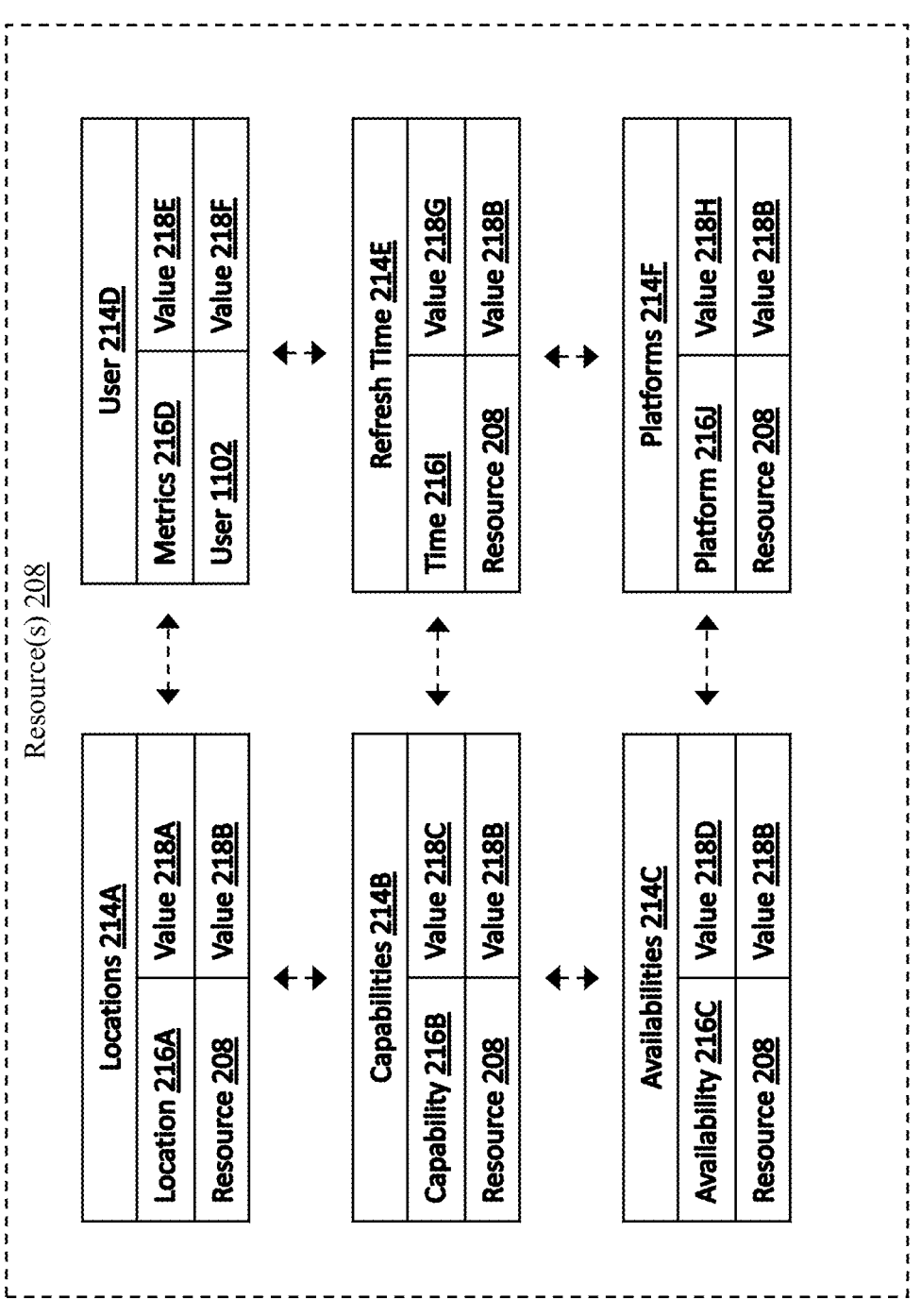
FIG. 10 depicts an example of resource objects in accordance with some embodiments of the present disclosure.

As shown in FIG. 10, resources 208 may be represented by one or more resource objects 214. For example, a resource object for locations 214A may identify at least one location 216A associated with the resource 208 (e.g., where the resource 208 may be accessed) with value 218A (e.g., zip code) and value 218B (e.g., identifier of the resource 208), respectively.

In some embodiments, one or more of the plurality of resource objects 214 that represent a respective resource of the plurality of resources 208 managed by the plurality of resource platforms 101 include a capability property (e.g., 216B) indicating the capability of the respective resource 208. In some embodiments, one or more of the plurality of resource objects 214 that represent the plurality of resources 208 managed by the plurality of resource platforms 101 may include the capability property mapped to the capability of the respective resource. For example, a resource object for capabilities 214B of the resource 208 may identify at least one capability 216B (e.g., whether the device is for child or adult) of the resource 208 with value 218C (e.g., scan setting, test number, weight limit, size limits) and value 218B, respectively.

In some embodiments, one or more of the plurality of resource objects 214 that represent a respective resource of the plurality of resources 208 managed by the plurality of resource platforms 101 include an availability property (e.g., 214C) indicating the availability of the respective resource 208. In some embodiments, one or more of the plurality of resource objects 214 that represent the plurality of resources 208 managed by the plurality of resource platforms 101 may include a respective resource value (e.g., 218B) mapped to the respective resource 208. In some embodiments, one or more of the plurality of resource objects 214 that represent the plurality of resources 208 managed by the plurality of resource platforms 101 may include the availability property mapped to the availability of the respective resource (e.g., value 218B). For example, a resource object for availabilities 214C of the resource 208 may identify at least one availability 216C (e.g., when the resource 208 can be utilized) of the resource 208 with value 218D (e.g., Friday at 9 am) and value 218B, respectively. In some embodiments, one or more of the plurality of resource objects 214 that represent a respective resource of the plurality of resources 208 managed by the plurality of resource platforms 101 include an availability property (e.g., 216C) indicating the availability of the respective resource and a capability property (e.g., 216B) indicating the capability of the respective resource 208.

In another example, a resource object for the user 214D may describe the metrics 216D (e.g., height, weight, and/or settings) of the user 1102 that is associated with the resource 208 (e.g., securing use of the resource 208) with value 218E (e.g., number of pounds) and value 218F (e.g., identifier), respectively. In another example, a resource object for refresh times 214E of the resource 208 may identify a time 216I (e.g., when the platform 101 was last accessed and/or when the resource object 214 expires) of the resource 208 with value 218G (e.g., timestamp) and value 218B, respectively. In another example, a resource object for platforms 214F associated with the resource 208 may identify at least one platform 216J (e.g., EHR A) that manages or is otherwise associated with the resource 208 with value 218H (e.g., identifier) and value 218B, respectively.

In another example, properties of the resource objects 214 may describe resources 208 such as a list of practices from the platform 101. In another example, properties of the resource objects 214 may describe resources 208 such as a list of departments from the platform 101. In another example, properties of the resource objects 214 may describe resources 208 such as patient information from the platform 101. In another example, properties of the resource objects 214 may describe a patient based on their ZIP code and date of birth. In another example, properties of the resource objects 214 may describe resources 208 such as provider information from the platform 101. In another example, properties of the resource objects 214 may describe resources 208 such as a list of providers from the list of providers in the platform 101.

The object mapping service 134 may generate the resource objects 214 from the normalized responses 212 for storage in resource cache 170. In some embodiments, the object mapping service 134 may generate the plurality of resource objects 214 for storage in the resource cache 170 using the respective mapping identifiers to map the attributes to the properties of the plurality of resource objects 214. For example, as shown in FIG. 12, in flow 1212, the interface gateway 120 may store the resource objects 214 in the resource cache 170. In some embodiments, the object mapping service 134 may generate, based on respective mapping identifiers for each respective resource platform 101 of the plurality of resource platforms 101, the plurality of resource objects 214 for storage in the resource cache 170 using the respective mapping identifiers to map the attributes to the properties of the plurality of resource objects 214.

In some embodiments, the interface gateway 120 may cause the administrator device 1110 of the administrator 1112 to display an example interface to configure the properties of the resource objects 214. For example, the interface gateway 120 may receive inputs to modify the address property of the resource objects 214 to modify the address of the resource 208 represented by the resource objects 214.

In some embodiments, the object mapping service 134 may be configured to handle numerous concurrent resource objects 214 that may be, but are not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000

(e.g., but not limited to, 100,000,000-999,999,999), at least 1,000,000,000 (e.g., but not limited to, 1,000,000,000-999,999,999,999), and so on.

The abstraction layer 130 may include a caching service 136 for interfacing with the resource cache 170. In some embodiments, the caching service 136 may access the resource cache 170 that includes the plurality of resource objects 214 representing the plurality of resources 208 managed by the plurality of resource platforms 101. The caching service 136 may communicate with the resource cache 170 via the cache API 160. The object mapping service 134 of the data integration system 100 may access the resource cache 170 via the cache API 160.

In some embodiments, the caching service 136 may store the resource objects 214 in the resource cache 170. In some embodiments, the caching service 136 may store, in the resource cache 170, a plurality of resource objects 214 for each resource platform 101. For example, the resource cache 170 storing the resource objects 214 may maintain a cached set of appointments. In some embodiments, the caching service 136 may store, responsive to the respective customized application programming interface call 206 to each of the plurality of resource platforms 101, in the resource cache 170, a plurality of resource objects 214 for each resource platform 101.

The resource cache 170 may include one or more caches, partitions, and/or logical storage units for storing the resource objects 214. In some embodiments, the resource cache 170 is one cache. In some embodiments, the resource cache 170 is one cache with multiple logical partitions that each store a respective type of the resource objects 214. In some embodiments, the resource cache 170 includes two or more separate caches. In some embodiments, the resource cache 170 includes a first cache for storing information about the platforms 101. For example, the first cache may include resource objects 214 with properties indicative of the resource 208 managed by the platforms 101. In some embodiments, the resource cache 170 includes a second cache for storing the appointment availability. For example, the resource objects 214 indicative of the appointment availability for utilizing the resources 208 may be stored in the second cache. In another example, the second cache may include the resource objects 214 with properties indicative of the availability (e.g., appointment availability) of the resources 208.

In some embodiments, the abstraction layer 130 may include a scheduling service 132 for scheduling updates of resource objects 214 that represent the resources 208. For example, the scheduling service 132 of the abstraction layer 130 may update the resource objects 214 that represent the resources 208. In some implementations, the scheduling service 132 may schedule the updates as batch refreshes of the resource objects 214 stored in the resource cache 170 via abstracted queries 204 to the normalization layer 140 that generates the customized application programming interface call 206 to the resource platforms 101. For example, the platform 101 may be an EHR company A or EHR company B for which a full and/or incremental refresh are supported. In some implementations, the scheduling service 132 may proactively request updates of the resource objects 214 in micro batches and/or small batch jobs. For example, the scheduling service 132 may frequently request the platforms 101 to provide 7 days of information about the resources 208.

In some embodiments, the scheduling service 132 may generate, periodically for each resource platform 101 of the plurality of resource platforms 101, according to at least one refresh period, at least one subsequent abstracted query 204 configured to synchronize the availability of the plurality of resources 208 between the resource orchestrator 122 and the plurality of resource platforms 101. For example, the scheduling service 132 may schedule the normalization layer 140 to transmit the customized application programming interface call 206 via the API 150 to platforms 101 at each refresh period. In some implementations, as shown in FIG. 11, the scheduling service 132 may use scheduling API rules 133 (e.g., Representational state transfer (REST) API) to schedule the customized application programming interface call 206 with the platforms 101.

In some embodiments, as shown in FIG. 12, in flow 1222, the interface gateway 120 may transmit the API call 206 to the platform 101 to refresh the resource objects 214. For example, if the resource object 214 describing the resource 208 is in the cache, the interface gateway 120 may transmit the API call 206 to the platform 101 to request the newest value associated with the resource 208. The scheduling service 132 may schedule the updates according to the refresh period to be at set times, every few minutes or hourly, daily, nightly, and/or weekly. In some embodiments, the at least one refresh period is one day. For example, the scheduling service 132 may schedule the updates outside of business hours. In another example, the scheduling service 132 may schedule frequent and small micro batch updates. In some embodiments, the refresh period can be unique to each platform 101, resource 208, location, date, or appointment.

In some embodiments, the platform identification service 142 may generate, based on the at least one refresh period, at least one subsequent respective customized application programming interface call 206 to each respective resource platform 101 by modifying at least one subsequent abstracted query 204 for each respective resource platform 101 of the plurality of resource platforms 101 based on each respective application programming interface of the plurality of application programming interfaces 150.

In some embodiments, as shown in FIG. 12, in flow 1224, the interface gateway 120 may receive the unstructured response 210 with attributes from which to refresh the resource objects 214. In some embodiments, the platform translation service 144 of the normalization layer 140 may receive an unstructured response 210 from the platforms 101 in response to the customized application programming interface call 206 associated with the refresh. The unstructured response 210 may include a resource identifier associated with a particular resource 208. In some embodiments, the platform translation service 144 may query, based on the unstructured response 210, the resource cache 170 to identify at least one existing resource object 214 associated with a particular resource identifier. The platform translation service 144 of the normalization layer 140 may generate a normalized response 212 from the unstructured response 210.

In some embodiments, as shown in FIG. 12, in flow 1226, the interface gateway 120 may compare the attributes in the normalized response 212 to the properties of the existing resource objects 214. In some embodiments, the caching service 136 may query, using the normalized response 212, the resource cache 170 to identify at least one existing resource object 214 associated with the particular resource identifier. In some embodiments, the caching service 136 may update the existing resource object 214 to store a particular availability and a particular capability associated with the particular resource identifier of the particular resource 208.

In some embodiments, as shown in FIG. 12, in flow 1228, if the attributes associated with a resource 208 has been refreshed, the interface gateway 120 can refresh the corresponding properties of the resource objects 214 in the cache 170. In some embodiments, the caching service 136 of the interface gateway 120 can update the properties of the resource objects 214. In some embodiments, the caching service 136 of the interface gateway 120 can version control the changes to the properties of the resource objects 214. For example, the caching service 136 can indicate when the properties were updated and to which version the updates correspond. In some embodiments, the caching service 136 can store previous properties and newly updated properties. For example, the caching service 136 can revert to older properties if the changes to the resources 208 are changed.

In some embodiments, the resource integration system 100 may store the plurality of refreshed resource objects 214 responsive to the at least one subsequent respective customized application programming interface call 206 to each of the plurality of resource platforms 101. In some embodiments, the caching service 136 may store, in the resource cache 170, a plurality of refreshed resource objects 214 for each resource platform 101.

In some embodiments, the plurality of refreshed resource objects 214 may include an up-to-date record (e.g., properties) of each resource of the plurality of resources 208 managed by the plurality of resource platforms 101. In some embodiments, the plurality of refreshed resource objects 214 may include the up-to-date record for changed resources of the plurality of resources 208. In some embodiments, the plurality of refreshed resource objects 214 may include the up-to-date record for the plurality of resources 208. In some embodiments, the up-to-date record may include an updated availability property indicating the current availability of the respective resource 208. In some embodiments, the up-to-date record may include an updated capability property indicating a current capability of the respective resource 208.

In some embodiments, the caching service 136 may identify the plurality of resource objects 214 in the resource cache 170 to satisfy an abstracted query 204 generated from a resource request 202 from the client device 102. For example, the resource objects 214 may already be updated and available in the resource cache 170 without necessitating a call to the resource platform 101. In some embodiments, the caching service 136 may determine, for each resource platform 101, the plurality of resource objects 214 associated with the abstracted query 204 based at least in part on the respective mapping identifiers of the resource objects 214.

In some embodiments, the caching service 136 may parse the attributes of the resource request 202 to identify associated and/or matching properties of the resource objects 214 to satisfy the resource request 202. For example, the caching service 136 may identify resource objects 214 with properties that indicate that a resource 208 is available at a time that matches the attribute of the requested time in the resource request 202. In some embodiments, the caching service 136 may determine a particular resource object of the plurality of resource objects 214 in the resource cache 170. In some embodiments, the data integration system 100 may determine a particular resource platform 101 associated with the particular resource object.

In some embodiments, the particular resource object may include at least one particular capability property. The particular resource object may represent a particular resource for the resource request 202. In some embodiments, the caching service 136 may determine at least one particular resource property representing at least one particular capability that corresponds to the at least one user attribute. In some embodiments, the caching service 136 may determine at least one particular resource property representing at least one particular capability that corresponds to the at least one requested capability defined by the at least one resource request attribute. In some embodiments, the caching service 136 may determine at least one particular resource property representing at least one particular capability that corresponds to the at least one user attribute and the at least one requested capability defined by the at least one resource request attribute.

In some embodiments, the interface gateway 120 may cause the client device 102 to display an example client interface with the templates of properties of the resource objects 214 retrieved responsive to a resource request 202 for a resource 208 such as for a healthcare provider resource. For example, as shown in FIG. 12, in flow 1214, the interface gateway 120 may transmit the resource objects 214 for display to the client device 102. In another example, as shown in FIG. 12, in flow 1218, the interface gateway 120 can transmit the indication if there are no resources 208 available to the client device 102. In another example, as shown in FIG. 12, in flow 1230, the interface gateway 120 may transmit the refreshed resource object 214 to the client device 102.

In some embodiments, the interface gateway 120 may transmit to the at least one client device 102, in real-time, a particular plurality of resource selection questionnaire templates specific to the particular resource platform 101. In some embodiments, the transmitted templates may cause the device 102 to display the particular plurality of resource selection questionnaire templates.

In some embodiments, the transmitted templates may cause the client device 102 to return at least one user input associated with the particular plurality of resource selection questionnaire templates. For example, the user inputs to select the resource 208 can be received via the interface. The abstraction layer 130 may receive user inputs from the client device 102 to secure a resource 208. In some embodiments, the transmitted templates may cause the interface gateway 120 to determine, based on the at least one user input, a particular availability of the particular resource object 214 associated with the resource 208 to be secured.

In some embodiments, the transmitted templates may cause the normalization layer 140 to generate, based on a particular application programming interface 150 of the particular resource platform 101 and the particular availability of the particular resource object 214, a particular application programming interface call 206 that includes at least one resource selection configured to cause the particular resource platform 101 to secure, for the user of the client device 102, the at least one resource 208 associated with the particular resource object 214. In some embodiments, the particular application programming interface call 206 may be similar to in structure and function as the customized application programming interface call 206.

The normalization layer 140 may, based on the user input received by the abstraction layer 130, transmit a particular normalized application programming interface call 206 to the particular resource platform 101 to cause the particular resource platform 101 to secure, for the user of the client device 102, the at least one resource 208 associated with the particular resource object 214. For example, the particular application programming interface call 206 can cause the platform 101 to reserve a particular machine at a particular time for utilization by the user of the client device 102. In another example, the particular application programming interface call 206 can cause the platform 101 to post a token to the platform 101. In another example, the particular application programming interface call 206 can cause the platform 101 to update an existing patient in the platform 101. In another example, the particular application programming interface call 206 can cause the platform 101 to create a new patient in the platform 101.

Figure 4:
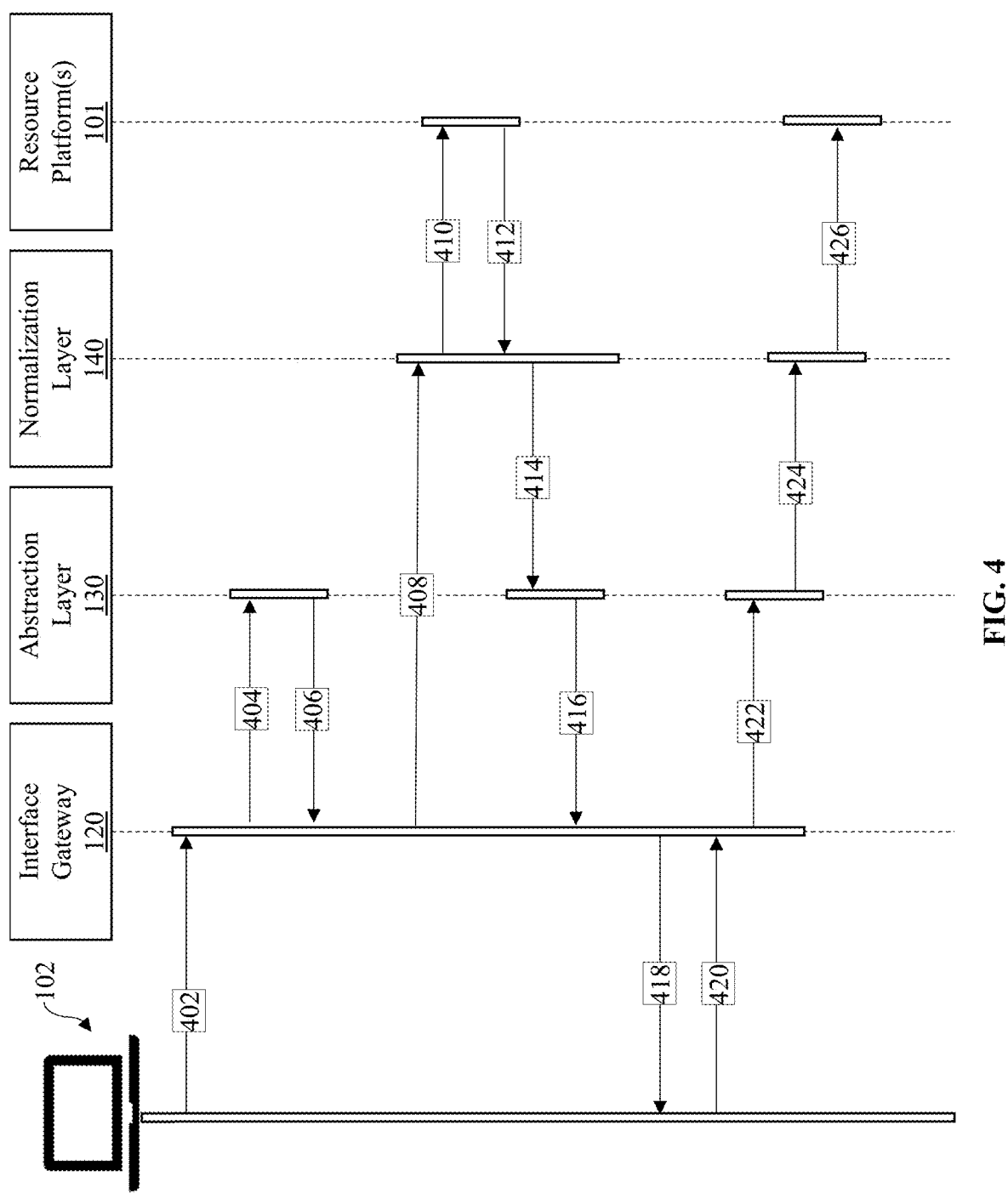
FIG. 4 depicts a messaging flow in an API gateway of a resource integration system in accordance with some embodiments of the present disclosure.

Referring to FIG. 4, a messaging flow in an API gateway of a resource integration system 100 is illustrated in accordance with some embodiments of the present disclosure. The resource integration system 100 is illustrated in accordance with some embodiments of the present disclosure. In some embodiments, a resource integration system 100 may include the interface gateway 120 with the abstraction layer 130 and a normalization layer 140 for communicating with the various resource platforms 101 that manage resources 208. The resources may be electronic representations of devices, machines, providers, and/or equipment. In some embodiments, the resources 208 may describe devices, machines, equipment, and/or healthcare providers.

The resource integration system 100 may manage resource objects 214 to standardize the representation of the resources 208. The resource integration system 100 may generate an abstract query 204 via the cache API 160 for properties (e.g., availability) of resource objects 214 in the resource cache 170. To obtain attributes about resources 208 from the platforms 101, the resource integration system 100 may normalize the abstract query 204 to generate a customized application programming interface call 206 (e.g., custom API call) for querying each platform 101 for attributes about the resources 208. For example, the resource integration system 100 may have the extensiveness and comprehensiveness to generate 3 API calls.

In response to the customized application programming interface call 206, the resource platforms 101 may respond with unstructured responses 210 that include the attributes about the resources 208. The resource integration system 100 may generate a normalized response 212 from the unstructured response 210. The resource integration system 100 may generate a resource object 214 from the normalized responses 212 for storage in resource cache 170. The resource integration system 100 may map the normalized responses 212 received in any format from any platform 101 into the resource object 214 fields of resource, availability, and capability. For example, the resource object 214 may identify the resource 208 and its availability (e.g., next Friday at 9 am) and capability (e.g., whether the device is for child or adult).

By having attributes from each platform 101 stored in the resource cache 170 as resource objects 214, the resource integration system 100 may handle resource requests 202 from the client devices 102 to utilize (e.g., schedule appointments) of the resources 208 of any platform 101. The resource integration system 100 may schedule the usage of resources 208 managed by any platform 101 to satisfy the resource requests 202. By determining a common denominator (e.g., abstracted query 204) of attributes that can be requested from the disparate platforms and generate the API calls (e.g., customized application programming interface call 206) that are dynamically adapted to any format that the resource platforms 101 may have based on the common denominator, the resource integration system 100 can obtain enriched attributes about the resources 208 from any of the resource platforms 101 in response to any resource request 202 from the client devices 102.

In step 402, a client device 102 may login to the resource integration system 100 via the endpoint interface 110. In some embodiments, the resource integration system 100 may include an interface gateway 120 configured to interface with at least one client device 102 and a plurality of resource platforms 101. In some embodiments, the plurality of resource platforms 101 may be a plurality of electronic health record (EHR) integrations. In some embodiments, the resource integration system 100 may implement computer engines for interacting with the client device 102 via the endpoint interface 110 to obtain resource requests 202 to construct an abstracted query 204. In some embodiments, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

The interface gateway 120 may include a resource orchestrator 122 that includes at least one processor in communication with at least one non-transitory computer-readable medium having software instructions stored thereon. In some embodiments, the resource orchestrator 122 may include hardware components such as a processor, which may include local or remote processing components. In some embodiments, the processor may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processor may include data-processing capacity provided by the microprocessor. In some embodiments, the microprocessor may include memory, processing, interface resources, controllers, and counters. In some embodiments, the microprocessor may also include one or more programs stored in memory.

The interface gateway 120 may include one or more data stores, including a directory and/or template library, such as one or more local and/or remote data storage solutions such as, e.g., local hard-drive, solid-state drive, flash drive, database or other local data storage solutions or any combination thereof, and/or remote data storage solutions such as a server, mainframe, database or cloud services, distributed database or other suitable data storage solutions or any combination thereof. In some embodiments, the data store(s) may include, e.g., a suitable non-transient computer readable medium such as, e.g., random access memory (RAM), read only memory (ROM), one or more buffers and/or caches, among other memory devices or any combination thereof.

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, the endpoint interface 110 may utilize one or more software computing interface technologies, such as, e.g., Common Object Request Broker Architecture (CORBA), an application programming interface (API) and/or application binary interface (ABI), among others or any combination thereof. In some embodiments, an API and/or ABI defines the kinds of calls or requests that can be made, how to make the calls, the data formats that should be used, the conventions to follow, among other requirements and constraints. An "application programming interface" or "API" can be entirely custom, specific to a component, or designed based on an industry-standard to ensure interoperability to enable modular programming through information hiding, allowing users to use the interface independently of the implementation. In some embodiments, CORBA may normalize the method-call semantics between application objects residing either in the same address-space (application) or in remote address-spaces (same host, or remote host on a network). In some embodiments, one or more interfaces may utilize one or more hardware computing interface technologies, such as, e.g., Universal Serial Bus (USB), IEEE 1394 (FireWire), Ethernet, Thunderbolt™, Serial ATA (SATA) (including eSATA, SATAe, SATAp, etc.), among others or any suitable combination thereof.

In some embodiments, the client device 102 may include one or more computing devices, including, e.g., at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth. For example, as shown in FIG. 11, the client device 102 may be a mobile device 1104 or a computer 1106.

In some embodiments, the client device 102 may communicate with the resource integration system 100 via the endpoint interface 110 to access data provided by one or more of the resource platforms 1, 2, 3 through n. In some embodiments, there may be a front-end client for each user type associated with the resource integration system 100. For example, a customer accessing data for personal user, a business accessing data for company, enterprise, employee, etc. use, an administrator accessing the resource integration system 100 for administration purposes, a platform owner accessing the resource platform(s) 1, 2, 3 through n, e.g., for configuring and/or development tasks, among other user types or any combination thereof.

For example, as shown in FIG. 11, the endpoint interface 110 may include the include API gateway 1108 for facilitating communications between the mobile device 1104 or the computer 1106 of the user 1102 and the resource integration system 100. In another example, as shown in FIG. 11, the endpoint interface 110 may include the API gateway 1108 that may facilitate communications between a provider portal 1114 of a provider 1116 (e.g., physician) and the resource integration system 100. In another example, as shown in FIG. 11, the endpoint interface 110 may include the API gateway 1108 that may facilitate communications between the administrator device 1110 of the administrator 1112 (e.g., insurance agent or medical administrator) and the resource integration system 100.

In some embodiments, the resource integration system 100 may receive attributes about the resources 208 from the administrator device 1110. For example, the resource integration system 100 may receive an import of the attributes of the resources 208 from which the resource integration system 100 may initialize or generate the resource objects 214 for storage in the resource cache 170. As further described below, the resource integration system 100 can communicate with the resource platforms 101 to update the existing resource objects 214 and add new resource objects 214.

Now referring to FIG. 9, in some embodiments, the client device 102 displays interfaces 900 for obtaining resource requests 202. For example, as shown in FIG. 11, the user 1102 may be a patient that interacts with the interfaces 900. In some embodiments, the endpoint interface 110 may enable access to the system 100 via one or more front-end client interfaces 900. For example, the front-end client interfaces 900 may include, e.g., a webpage, a native application on one or more operating systems, a message adapter, a software development kit (SDK), a terminal/thin client, or other front-end client or any combination thereof.

For example, as shown in FIG. 12, in flow 1202, the interface gateway 120 may receive a resource request 202 from the client device 102. In some embodiments, when attempting to access data provided by one or more of the resource platforms 1, 2, 3 through n 101, the user 1102 may communicate from the client device 102 with the resource integration system 100 via an endpoint interface 110 to define a resource request 202. For example, the client device 102 may receive interactions from the user 1102 via the interface 900 for submitting a resource request 202 including a healthcare provider resource.

In some embodiments, the resource requests 202 can include a resource request attribute defining at least one requested capability of the resource 208. For example, the interfaces 900 may include user interface elements 902 that are user selectable and/or user input fields for defining resource request attributes of the resource request 202. In some embodiments, the resource request 202 includes at least one user attribute associated with the user 1102 of the client device 102. For example, the user attribute can be an identifier that identifies the user 1102. The resource requests 202 may be transmitted from the client device 102 to the interface gateway 120 via the endpoint interface 110. The interface gateway 120 may receive the resource requests 202. In some embodiments, the interface gateway 120 receives from the at least one client device 102, the resource request 202 representing at least one request for at least one resource of the plurality of resources.

In some embodiments, to dynamically generate prompts in the interface 900 to obtain the resource requests 202, the resource integration system 100 may include computer engines including, e.g., a questionnaire service. In some embodiments, the questionnaire service may include dedicated and/or shared software components, hardware components, or a combination thereof. For example, the questionnaire service may include a dedicated processor and storage. However, in some embodiments, the questionnaire service may share hardware resources, including the processor of the resource orchestrator 122 of the interface gateway 120.

The interface gateway 120 may include an abstraction layer 130 and a normalization layer 140 to provide improved integration of data from resource platforms 1, 2, 3 through n 101. In some embodiments, the interface gateway 120 may be an API management tool that sits between the client device 102 and one or more backend services, including resource platforms 101. In some embodiments, the interface gateway 120 may include one or more software-based services to provide software security, data communication/message routing, rate limiting, user authentication, error detection, system monitoring and/or analytics, as well as API orchestration and management, among other functionalities or any combination thereof. For example, authentication with the platforms 101 may be based on API Keys, Open Authorization (OAUTH), and/or Fast Healthcare Interoperability Resources (FIHR).

In step 404, the client device 102 may cause, via the endpoint interface 110, the interface gateway 120 to search for a resource 208 via the abstraction layer 130. In some embodiments, the abstraction layer 130 and the normalization layer 140 may enable access to APIs 1, 2, 3 through n 150 associated with the resource platforms 1, 2, 3 through n 101 using common format ("abstracted") API calls or queries (e.g., abstracted query 204). For example, as shown in FIG. 12, in flow 1204, the interface gateway 120 may transmit an abstract query 204 to the resource cache 170 to identify resource objects 214 to satisfy the resource request 202. In some embodiments, the abstraction layer 130 may map resource requests 202 to a common format ("abstracted") query or API call that includes data common to each API 1, 2, 3 through n 150. In some embodiments, the abstraction layer 130 may generate an abstracted query 204 about a plurality of resources 208 managed by the plurality of resource platforms 101.

In step 406, the abstraction layer 130 may generate the abstract query 204. In some embodiments, the abstraction layer 130 may use attributes provided by the resource request 202 to structure the abstracted query 204. In some embodiments, the abstraction layer 130 may generate the abstracted query 204 for each respective resource of the plurality of resources 208. In some embodiments, the abstraction layer 130 may generate the abstracted query 204 for an availability of each respective resource of the plurality of resources 208. In some embodiments, the abstraction layer 130 may generate the abstracted query 204 for a capability of each respective resource of the plurality of resources 208.

In step 408, the abstraction layer 130 may transmit the abstract query 204. In some embodiments, the abstraction layer 130 may generate the abstracted query 204 to query the cache 170 for the resources 208 represented by the resource objects 214. For example, as shown in FIG. 12, in flow 1206, the interface gateway 120 may determine that the cache 170 does not have any resource objects 214 for resources 208 to satisfy the resource request 202. For example, in some embodiments, the interface gateway 120 may receive the resource request 202 from the client device 102 of the user. The resource request 202 may include a resource attribute defining a requested resource 208. The abstraction layer 130 may query, using the at least one resource attribute, the resource cache 170 to identify at least one resource object 214 having at least one capability matching the at least one resource attribute in response to the resource request 202.

In some embodiments, the abstraction layer 130 may query, using a plurality of resource attributes, the resource cache 170 to identify at least one resource object 214 having at least one capability matching the at least one resource attribute in response to the resource request 202, including multiple resource attributes, one or more resource attributes according to multiple properties, compound resource attributes (e.g., a resource attribute formed from multiple sub-attributes) or any other combination of resource attributes and/or properties thereof. For example, the abstraction layer 130 may query numerous attributes to identify one or more resource objects 214 that have matching properties. In some embodiments, the abstraction layer 130 may determine that the resource object 214 is not present in the resource cache 170.

If the resource objects 214 are unavailable in the cache 280, the abstraction layer 130 may transmit the abstracted query 204 to the normalization layer 140. For example, as shown in FIG. 12, in flow 1208, the interface gateway 120 may transmit the API call 206 to the platforms 101 associated with the resources 208.

Conversely, for example, as shown in FIG. 12, in flow 1220, the interface gateway 120 may determine that the cache 170 has resource objects 214 for resources 208 to satisfy the resource request 202. If the cache 170 has the resource objects 214 that are available, the interface gateway 120 may transmit the resource objects. The normalization layer 140 may communicate, based on the at least one resource object 214 for display as shown in flow 1230 not being present in the resource cache 170, the resource request 202 to a platform via a resource platform 101. The normalization layer 140 may receive, from the platform, at least one resource assignment reserving at least one resource 208 for the user. For example, if the resource object 214 describing the resource 208 is not in the cache, the normalization layer 140 may return, from the platform 101, the newest value associated with the resource 208.

In step 410, the normalization layer 140 may generate the customized application programming interface call 206 to the resource platform 101. In some embodiments, the platform identification service 142 of the normalization layer 140 of the interface gateway 120 may generate a respective customized application programming interface call 206 to each respective resource platform 101 by modifying the abstracted query 204 for each respective resource platform 101 of the plurality of resource platforms 101. The customized application programming interface call 206 may be formatted to be compatible with the platforms 101 so that the platforms 101 may respond with attributes about the resource 208.

In some embodiments, as shown in Table 1 above, the interface gateway 120 may generate the customized application programming interface calls 206 to transmit (e.g., post) an authentication token to the platform 101. For example, the authentication token may be a security key that enables the interface gateway 120 to access the platform 101.

In some embodiments, as shown in Table 2 above, the interface gateway 120 may generate the customized application programming interface calls 206 to request (e.g., get) attributes about the resources 208 managed by the platforms 101 (e.g., EHR). For example, the customized application programming interface calls 206 may request a list of practices managed by the platforms 101. In another example, the customized application programming interface calls 206 may request a list of departments managed by the platforms 101. In some implementations, the interface gateway 120 may generate the customized application programming interface calls 206 in response to a resource request 202 received from the administrator device 1110 of the administrator 1112. For example, the administrator 1112 may want to access the resources 208 to see what is available for the user 1102.

In some embodiments, as shown in Table 3 above, the interface gateway 120 may generate the customized application programming interface calls 206 to request (e.g., get) attributes about the user 1102 (e.g., patient) from the platforms 101 (e.g., EHR). For example, the customized application programming interface calls 206 may request patient information from the platforms 101. In another example, the customized application programming interface calls 206 may request attributes of the user 1102 based on their date of birth and zip code. In some embodiments, the interface gateway 120 may generate the customized application programming interface calls 206 to modify (e.g., put) attributes about the user 1102 (e.g., patient) stored by the platforms 101. For example, the customized application programming interface calls 206 may update an existing patient in the platforms 101. In some embodiments, the interface gateway 120 may generate the customized application programming interface calls 206 to transmit (e.g., post) attributes about the user 1102 (e.g., patient) that is new to the platforms 101. For example, the customized application programming interface calls 206 may create a new patient in the platforms 101. In some implementations, the interface gateway 120 may generate the customized application programming interface calls 206 in response to a resource request 202 received by the interface gateway 120 from the mobile device 1104 or the computer 1106 of the user 1102. For example, the user 1102 may want to access the resources 208 associated with their own attributes such as demographic information.

In some embodiments, as shown in Table 4 above, the interface gateway 120 may generate the customized application programming interface calls 206 to request (e.g., get) properties about the resources 208 (e.g., devices of a provider) from the platforms 101 (e.g., EHR). For example, the customized application programming interface calls 206 may request patient information from the platforms 101. In another example, the customized application programming interface calls 206 may request attributes of the user 1102 based on their date of birth and zip code. In some implementations, the interface gateway 120 may generate the customized application programming interface calls 206 in response to a resource request 202 received by the interface gateway 120 from the provider portal 1114 of the provider 1116. For example, the provider 1116 may want to access the resources 208 to see attributes of resources 208 associated with the provider 1116.

In some embodiments, the platform identification service 142 may determine a set of additional application programming interface fields in each respective customized application programming interface call 206. For example, the additional application programming interface fields may be for communicating with a particular platform 101. The set of additional application programming interface fields may be in addition to a set of abstracted query fields of the abstracted query 204. The set of abstracted query fields may define each respective resource of the plurality of resources 208. Examples of fields may also include Date of Birth (DOB), Department, Email, Guarantor Email, SSN, Home Phone, Mobile Phone, Work Phone, and/or ZIP Code.

In some embodiments, the object mapping service 134 may determine a set of additional application programming interface data for each respective customized application programming interface call 206 to populate the set of additional application programming interface fields based at least in part on the plurality of resource objects 214 associated with the abstracted query 204. In some embodiments, the resource integration system 100 may generate the respective customized application programming interface call 206 to each respective resource platform 101 by modifying the abstracted query 204 for each respective resource platform of the plurality of resource platforms 101 to include the set of additional application programming interface fields comprising the set of additional application programming interface data of each respective customized application programming interface call 206.

In some embodiments, the platform identification service 142 may generate the customized application programming interface call 206 based on the APIs 150. In some implementations, as shown in FIG. 11, the platform identification service 142 may use API generation rules 143 (e.g., Representational state transfer (REST) API) to generate the customized application programming interface call 206 with the platforms 101. In some embodiments, each of API 1 150, API 2 150, API 3 150 through API n 101 may include one or more APIs associated with a corresponding resource platform 1 101, resource platform 2 101, resource platform 3 101 through resource platform n 101. For example, the API(s) of each API 1, 2, 3 through n 150 may include, e.g., any definition of the kinds of calls or requests that can be made, how to make the calls, the data formats that should be used, the conventions to follow, among other requirements and constraints.

In some embodiments, the API(s) of each API 1, 2, 3 through n 150 may be entirely custom, specific to a component, or designed based on an industry-standard to ensure interoperability to enable modular programming through information hiding, allowing users to use the interface 150 independently of the implementation. In some embodiments, one or more other software and/or hardware interfaces may be employed in addition to or instead of one or more of API 1, 2, 3 through n 150. Additionally, or alternatively, the APIs 150 may include support for a procedure call (RPC), which can be when the APIs 150 cause a procedure (e.g., subroutine) to execute in a different address space (e.g., resource platforms 101), such as to facilitate the customized application programming interface call 206 to the resource platform 101 or receive the unstructured responses 210 from the platforms 101. Examples of API formats/structures may include, e.g., representation state transfer (REST) (e.g., Fast Healthcare Interoperability Resources (FHIR) or other RESTful protocol or combination thereof), Simple Object Access Protocol (SOAP), server application programming interface (SAPI), or other API technology or any combination thereof. In some embodiments, the APIs 1, 2, 3 through n 150 may have various structures and/or data field requirements. For example, based on each client 102, the API 150 may be customized with authentication requirements, permissions, and/or API functions associated with each user type.

In some embodiments, the platform identification service 142 may identify or select a plurality of APIs 150 maintained by the normalization layer 140 for querying the plurality of resource platforms 101 about the plurality of resources 208 managed by the plurality of resource platforms 101. For example, as shown in FIG. 11, the APIs 150 may be included in the normalization layer 140 for facilitating communications between the integration system 100 and the platforms 101. In some embodiments, the resource integration system 100 may identify three APIs. For example, one API for each platform 101.

In some embodiments, the interface gateway 120 may catalog the structures and/or requirements of each API 1, 2, 3 through n 150 integrated on the resource integration system 100, and the abstraction layer 130 use the catalog of structures and/or requirements to determine a common denominator of information that is common to all APIs. For example, where each resource platform 1, 2, 3 through n 101 provide data for a particular context (e.g., merchant data, healthcare provider data, health records, multimedia, etc.), each resource platform 1, 2, 3 through n 101 may employ one or more respective APIs 1, 2, 3 through n 150 to define requested data.

In some embodiments, the plurality of APIs 150 may be defined by a plurality of resource selection questionnaire templates specific to each respective resource platform of the plurality of resource platforms 101. The resource integration system 100 may store the questionnaire templates in a template library 123. In some embodiments, the platform identification service 142 dynamically returns questionnaires based on the template questionnaires in the template library 123. The template questionnaires may include resource platform-specific templates for structuring the customized application programming interface call 206 based on the abstract queries 204.

The platform identification service 142 may adapt the abstracted query 204 to a resource platform 101 having multiple APIs associated therewith. For example, the normalization layer 140 may adapt the abstracted query 204 for each resource platform 101 depending on its respective API 150. Where a particular one or more of API 1 140, API 2 140, API 3 140 through API n 101 include multiple APIs for a corresponding resource platform 1 101, resource platform 2 101, resource platform 3 101 through resource platform n 101, the normalization layer 140 may translate the abstracted query 204 into a customized application programming interface call 206 that is particular for one or more of the APIs 150.

In some embodiments, the platform identification service 142 may generate a respective customized application programming interface call 206 to each respective resource platform 101 by modifying the abstracted query 204 for each respective resource platform 101 of the plurality of resource platforms 101 based on each respective application programming interface of the plurality of application programming interfaces 150. For example, the platform identification service 142 may translate the abstracted query 204 into customized application programming interface call 206 that are resource platform-specific API calls associated with each API 1, 2, 3 through n 150. In some embodiments, the platform identification service 142 may generate the customized application programming interface call 206 for a particular resource platform 101 based on the questionnaire templates associated with the APIs 150 associated with that resource platform 101.

In step 412, the normalization layer 140 may receive an unstructured response 210 from the platforms 101. In some embodiments, the platform translation service 144 of the normalization layer 140 may receive an unstructured response 210 from the platforms 101. For example, as shown in FIG. 11, the interface gateway 120 may communicate via a provider portal 1114 with a provider 1116 (e.g., physician) that provides attributes about the resources 208. In some embodiments, the platform translation service 144 may receive the unstructured response 210 from each of the plurality of resource platforms 101 via the APIs 150 in response to the customized application programming interface call 206.

In some embodiments, as shown in FIG. 12, in flow 1210, the interface gateway 120 may receive the unstructured response 210 from the platform 101 with attributes about the resource 208. For example, the unstructured response 210 may include a list of practices from the platform 101. In another example, the unstructured response 210 may include a list of departments from the platform 101. In another example, the unstructured response 210 may include patient information from the platform 101. In another example, the unstructured response 210 may include a patient based on their ZIP code and date of birth. In another example, the unstructured response 210 may include provider information from the platform 101. In another example, the unstructured response 210 may include a list of providers from the list of providers in the platform 101.

In some embodiments, the platform translation service 144 may receive the unstructured response 210 responsive to the respective customized application programming interface call 206 to each of the plurality of resource platforms 101. In some embodiments, the unstructured response 210 may include attributes indicative of the respective resource 208. In some embodiments, the unstructured response 210 may be indicative of the availability of the respective resource 208. In some embodiments, the unstructured response 210 may be indicative of the capability of the respective resource 208. In some embodiments, the unstructured response 210 may indicate that there aren't any resources 208 of the platforms 101 that can satisfy the resource request 202. For example, as shown in FIG. 12, in flow 1216, the interface gateway 120 may receive an unstructured response 210 from the platform 101 that indicates that there are no resources 208 that can satisfy the resource request 202. For example, the unstructured response 210 from the platform 101 may indicate that the resource 208 is unavailable or not found.

In step 414, the normalization layer 140 may transmit a normalized response 212 to the abstraction layer 130. The platform translation service 144 of the normalization layer 140 may generate a normalized response 212 from the unstructured response 210. The platform translation service 144 may map the normalized responses 212 received in any format from any platform 101 into the normalized response 212 fields of resource, availability, and capability. For example, the normalized response 212 may identify the resource 208 and its availability (e.g., next Friday at 9 am) and capability (e.g., whether the device is for child or adult). In another example, the normalized response 212 may include a list of practices from the platform 101. In another example, the normalized response 212 may include a list of departments from the platform 101. In another example, the normalized response 212 may include patient information from the platform 101. In another example, the normalized response 212 may include a patient based on their ZIP code and date of birth. In another example, the normalized response 212 may include provider information from the platform 101. In another example, the normalized response 212 may include a list of providers from the list of providers in the platform 101.

In step 416, the abstraction layer 130 may store a resource object 214 based on the normalized response 212. The abstraction layer 130 may include an object mapping service 134 that may map the normalized response 212 to resource objects 214. The object mapping service 134 may generate a resource object 214 from the normalized responses 212 for storage in resource cache 170. The object mapping service 134 may map the attributes in the normalized responses 212 from the resource platforms 101 to the resource objects 214 by linking the attributes to properties of the resource objects 214. Each of the resource objects 214 may include one or more properties 216 with one or more corresponding values 218 to describe the resources 208. The resources 208 may be electronic representations of devices, machines, providers, and/or equipment. In some embodiments, the resources 208 may describe devices, machines, equipment, and/or health-care providers. In some embodiments, the resource objects 214 may be standardized representations of the resources 208. For example, the resource objects 214 may be electronic representations of devices, machines, providers, and/or equipment. In some embodiments, the resource objects 214 may describe devices, machines, equipment, and/or healthcare providers.

As shown in FIG. 10, resources 208 may be represented by one or more resource objects 214. For example, a resource object for locations 214A may identify at least one location 216A associated with the resource 208 (e.g., where the resource 208 may be accessed) with value 218A (e.g., zip code) and value 218B (e.g., identifier of the resource 208), respectively.

In some embodiments, one or more of the plurality of resource objects 214 that represent a respective resource of the plurality of resources 208 managed by the plurality of resource platforms 101 include a capability property (e.g., 216B) indicating the capability of the respective resource 208. In some embodiments, one or more of the plurality of resource objects 214 that represent the plurality of resources 208 managed by the plurality of resource platforms 101 may include the capability property mapped to the capability of the respective resource. For example, a resource object for capabilities 214B of the resource 208 may identify at least one capability 216B (e.g., whether the device is for child or adult) of the resource 208 with value 218C (e.g., scan setting, test number, weight limit, size limits) and value 218B, respectively.

In some embodiments, one or more of the plurality of resource objects 214 that represent a respective resource of the plurality of resources 208 managed by the plurality of resource platforms 101 include an availability property (e.g., 214C) indicating the availability of the respective resource 208. In some embodiments, one or more of the plurality of resource objects 214 that represent the plurality of resources 208 managed by the plurality of resource platforms 101 may include a respective resource value (e.g., 218B) mapped to the respective resource 208. In some embodiments, one or more of the plurality of resource objects 214 that represent the plurality of resources 208 managed by the plurality of resource platforms 101 may include the availability property mapped to the availability of the respective resource (e.g., value 218B). For example, a resource object for availabilities 214C of the resource 208 may identify at least one availability 216C (e.g., when the resource 208 can be utilized) of the resource 208 with value 218D (e.g., Friday at 9 am) and value 218B, respectively. In some embodiments, one or more of the plurality of resource objects 214 that represent a respective resource of the plurality of resources 208 managed by the plurality of resource platforms 101 include an availability property (e.g., 216C) indicating the availability of the respective resource and a capability property (e.g., 216B) indicating the capability of the respective resource 208.

In another example, a resource object for the user 214D may describe the metrics 216D (e.g., height, weight, and/or settings) of the user 1102 that is associated with the resource 208 (e.g., securing use of the resource 208) with value 218E (e.g., number of pounds) and value 218F (e.g., identifier), respectively. In another example, a resource object for refresh times 214E of the resource 208 may identify a time 216I (e.g., when the platform 101 was last accessed and/or when the resource object 214 expires) of the resource 208 with value 218G (e.g., timestamp) and value 218B, respectively. In another example, a resource object for platforms 214F associated with the resource 208 may identify at least one platform 216J (e.g., EHR A) that manages or is otherwise associated with the resource 208 with value 218H (e.g., identifier) and value 218B, respectively.

In another example, properties of the resource objects 214 may describe resources 208 such as a list of practices from the platform 101. In another example, properties of the resource objects 214 may describe resources 208 such as a list of departments from the platform 101. In another example, properties of the resource objects 214 may describe resources 208 such as patient information from the platform 101. In another example, properties of the resource objects 214 may describe a patient based on their ZIP code and date of birth. In another example, properties of the resource objects 214 may describe resources 208 such as provider information from the platform 101. In another example, properties of the resource objects 214 may describe resources 208 such as a list of providers from the list of providers in the platform 101.

The object mapping service 134 may generate the resource objects 214 from the normalized responses 212 for storage in resource cache 170. In some embodiments, the object mapping service 134 may generate the plurality of resource objects 214 for storage in the resource cache 170 using the respective mapping identifiers to map the attributes to the properties of the plurality of resource objects 214. For example, as shown in FIG. 12, in flow 1212, the interface gateway 120 may store the resource objects 214 in the resource cache 170. In some embodiments, the object mapping service 134 may generate, based on respective mapping identifiers for each respective resource platform 101 of the plurality of resource platforms 101, the plurality of resource objects 214 for storage in the resource cache 170 using the respective mapping identifiers to map the attributes to the properties of the plurality of resource objects 214.

In some embodiments, the interface gateway 120 may cause the administrator device 1110 of the administrator 1112 to display an example interface to configure the properties of the resource objects 214. For example, the interface gateway 120 may receive inputs to modify the address property of the resource objects 214 to modify the address of the resource 208 represented by the resource objects 214.

In some embodiments, the object mapping service 134 may be configured to handle numerous concurrent resource objects 214 that may be, but are not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

The abstraction layer 130 may include a caching service 136 for interfacing with the resource cache 170. In some embodiments, the caching service 136 may access the resource cache 170 that includes the plurality of resource objects 214 representing the plurality of resources 208 managed by the plurality of resource platforms 101. The caching service 136 may communicate with the resource cache 170 via the cache API 160. The object mapping service 134 of the data integration system 100 may access the resource cache 170 via the cache API 160.

The caching service 136 may store the resource objects 214 in the resource cache 170. In some embodiments, the caching service 136 may store, in the resource cache 170, a plurality of resource objects 214 for each resource platform 101. For example, the resource cache 170 storing the resource objects 214 may maintain a cached set of appointments. In some embodiments, the caching service 136 may store, responsive to the respective customized application programming interface call 206 to each of the plurality of resource platforms 101, in the resource cache 170, a plurality of resource objects 214 for each resource platform 101.

The resource cache 170 may include one or more caches, partitions, and/or logical storage units for storing the resource objects 214. In some embodiments, the resource cache 170 is one cache. In some embodiments, the resource cache 170 is one cache with multiple logical partitions that each store a respective type of the resource objects 214. In some embodiments, the resource cache 170 includes two or more separate caches. In some embodiments, the resource cache 170 includes a first cache for storing information about the platforms 101. For example, the first cache may include resource objects 214 with properties indicative of the resource 208 managed by the platforms 101. In some embodiments, the resource cache 170 includes a second cache for storing the appointment availability. For example, the resource objects 214 indicative of the appointment availability for utilizing the resources 208 may be stored in the second cache. In another example, the second cache may include the resource objects 214 with properties indicative of the availability (e.g., appointment availability) of the resources 208.

The abstraction layer 130 may include a scheduling service 132 for scheduling updates of resource objects 214 that represent the resources 208. For example, the scheduling service 132 of the abstraction layer 130 may update the resource objects 214 that represent the resources 208. In some implementations, the scheduling service 132 may schedule the updates as batch refreshes of the resource objects 214 stored in the resource cache 170 via abstracted queries 204 to the normalization layer 140 that generates the customized application programming interface call 206 to the resource platforms 101. For example, the platform 101 may be an EHR company A or EHR company B for which a full and/or incremental refresh are supported. In some implementations, the scheduling service 132 may proactively request updates of the resource objects 214 in micro batches and/or small batch jobs. For example, the scheduling service 132 may frequently request the platforms 101 to provide 7 days of information about the resources 208.

In some embodiments, the scheduling service 132 may generate, periodically for each resource platform 101 of the plurality of resource platforms 101, according to at least refresh period, at least one subsequent abstracted query 204 configured to synchronize the availability of the plurality of resources 208 between the resource orchestrator 122 and the plurality of resource platforms 101. For example, the scheduling service 132 may schedule the normalization layer 140 to transmit the customized application programming interface call 206 via the API 150 to platforms 101 at each refresh period. In some implementations, as shown in FIG. 11, the scheduling service 132 may use scheduling API rules 133

(e.g., Representational state transfer (REST) API) to schedule the customized application programming interface call 206 with the platforms 101.

In some embodiments, as shown in FIG. 12, in flow 1222, the interface gateway 120 may transmit the API call 206 to the platform 101 to refresh the resource objects 214. For example, if the resource object 214 describing the resource 208 is in the cache, the interface gateway 120 may transmit the API call 206 to the platform 101 to request the newest value associated with the resource 208. The scheduling service 132 may schedule the updates to be at set times, every few minutes or hourly, daily, nightly, and/or weekly. In some embodiments, the at least one refresh period is one day. For example, the scheduling service 132 may schedule the updates outside of business hours. In some embodiments, the scheduling service 132 may schedule frequent and small micro batch updates. For example, the scheduling service 132 may schedule updates that last 7 days. In some embodiments, the refresh period can be unique to each platform 101, resource 208, location, date, or appointment.

In some embodiments, the platform identification service 142 may generate, based on the at least refresh period, at least one subsequent respective customized application programming interface call 206 to each respective resource platform 101 by modifying at least one subsequent abstracted query 204 for each respective resource platform 101 of the plurality of resource platforms 101 based on each respective application programming interface of the plurality of application programming interfaces 150.

In some embodiments, as shown in FIG. 12, in flow 1224, the interface gateway 120 may receive the unstructured response 210 with attributes from which to refresh the resource objects 214. In some embodiments, the platform translation service 144 of the normalization layer 140 may receive an unstructured response 210 from the platforms 101 in response to the customized application programming interface call 206 associated with the refresh. The unstructured response 210 may include a resource identifier associated with a particular resource 208. In some embodiments, the platform translation service 144 may query, based on the unstructured response 210, the resource cache 170 to identify at least one existing resource object 214 associated with a particular resource identifier. The platform translation service 144 of the normalization layer 140 may generate a normalized response 212 from the unstructured response 210.

In some embodiments, as shown in FIG. 12, in flow 1226, the interface gateway 120 may compare the attributes in the normalized response 212 to the properties of the existing resource objects 214. In some embodiments, the caching service 136 may query, using the normalized response 212, the resource cache 170 to identify at least one existing resource object 214 associated with the particular resource identifier. In some embodiments, the caching service 136 may update the existing resource object 214 to store a particular availability and a particular capability associated with the particular resource identifier of the particular resource 208.

In some embodiments, as shown in FIG. 12, in flow 1228, if the attributes associated with a resource 208 has been refreshed, the interface gateway 120 can refresh the corresponding resource object 214 in the cache 170. In some embodiments, the caching service 136 of the interface gateway 120 can update the properties of the resource objects 214. In some embodiments, the caching service 136 of the interface gateway 120 can version control the changes to the properties of the resource objects 214. For example, the caching service 136 can indicate when the properties were updated and to which version the updates correspond. In some embodiments, the caching service 136 can store previous properties and newly updated properties. For example, the caching service 136 can revert to older properties if the changes to the resources 208 are changed.

In some embodiments, the resource integration system 100 may store the plurality of refreshed resource objects 214 responsive to the at least one subsequent respective customized application programming interface call 206 to each of the plurality of resource platforms 101. In some embodiments, the caching service 136 may store, in the resource cache 170, a plurality of refreshed resource objects 214 for each resource platform 101.

The plurality of refreshed resource objects 214 may include an up-to-date record (e.g., properties) of each resource of the plurality of resources 208 managed by the plurality of resource platforms 101. In some embodiments, the plurality of refreshed resource objects 214 may include the up-to-date record for changed resources of the plurality of resources 208. In some embodiments, the plurality of refreshed resource objects 214 may include the up-to-date record for the plurality of resources 208. In some embodiments, the up-to-date record may include an updated availability property indicating the current availability of the respective resource 208. In some embodiments, the up-to-date record may include an updated capability property indicating a current capability of the respective resource 208.

The caching service 136 may identify the plurality of resource objects 214 in the resource cache 170 to satisfy an abstracted query 204 generated from a resource request 202 from the client device 102. For example, the resource objects 214 may already be updated and available in the resource cache 170 without necessitating a call to the resource platform 101. In some embodiments, the caching service 136 may determine, for each resource platform 101, the plurality of resource objects 214 associated with the abstracted query 204 based at least in part on the respective mapping identifiers of the resource objects 214.

The caching service 136 may parse the attributes of the resource request 202 to identify associated and/or matching properties of the resource objects 214 to satisfy the resource request 202. For example, the caching service 136 may identify resource objects 214 with properties that indicate that a resource 208 is available at a time that matches the attribute of the requested time in the resource request 202. In some embodiments, the caching service 136 may determine a particular resource object of the plurality of resource objects 214 in the resource cache 170. In some embodiments, the data integration system 100 may determine a particular resource platform 101 associated with the particular resource object.

The particular resource object may include at least one particular capability property. The particular resource object may represent a particular resource for the resource request 202. In some embodiments, the caching service 136 may determine at least one particular resource property representing at least one particular capability that corresponds to the at least one user attribute. In some embodiments, the caching service 136 may determine at least one particular resource property representing at least one particular capability that corresponds to the at least one requested capability defined by the at least one resource request attribute. In some embodiments, the caching service 136 may determine at least one particular resource property representing at least one particular capability that corresponds to the at least one user attribute and the at least one requested capability defined by the at least one resource request attribute.

In step 418, the interface gateway 120 may cause the client device 102 to display interfaces based on the resource objects 214. In some embodiments, the interface gateway 120 may cause the client device 102 to display an example client interface with the templates of properties of the resource objects 214 retrieved responsive to a resource request 202 for a resource 208 such as for a healthcare provider resource. For example, as shown in FIG. 12, in flow 1214, the interface gateway 120 may transmit the resource objects 214 for display to the client device 102. In another example, as shown in FIG. 12, in flow 1218, the interface gateway 120 can transmit the indication if there are no resources 208 available to the client device 102. In another example, as shown in FIG. 12, in flow 1230, the interface gateway 120 may transmit the refreshed resource object 214 to the client device 102.

In some embodiments, the interface gateway 120 may transmit to the at least one client device 102, in real-time, a particular plurality of resource selection questionnaire templates 002 specific to the particular resource platform 101. In some embodiments, the transmitted templates may cause the device 102 to display the particular plurality of resource selection questionnaire templates.

In step 420, the interface gateway 120 may cause the client device 102 to provide an input in the interfaces. In some embodiments, the transmitted templates may cause the client device 102 to return at least one user input associated with the particular plurality of resource selection questionnaire templates. For example, the user inputs to select the resource 208 can be received via the interface. In some embodiments, the transmitted templates may cause the interface gateway 120 to determine, based on the at least one user input, a particular availability of the particular resource object 214.

In step 422, the abstraction layer 130 may receive user inputs from the client device 102 to secure a resource 208. In some embodiments, the transmitted templates may cause the client device 102 to return at least one user input associated with the particular set of resource selection questionnaire templates. For example, the user inputs to select the resource 208 can be received via the interface. The abstraction layer 130 may receive user inputs from the client device 102 to secure a resource 208. In some embodiments, the transmitted templates may cause the abstraction layer 130 to determine, based on the at least one user input, a particular availability of the particular resource object 214 associated with the resource 208 to be secured.

In step 424, the abstraction layer 130 may abstract the user inputs to the normalization layer 140. In some embodiments, the normalization layer 140 may determine a resource platform 101 associated with the at least one resource object 214 based at least in part on at least one resource platform identifier linked to the resource object 214.

In step 426, the normalization layer 140 may communicate with the resource platform 101 to secure the resource 208. The normalization layer 140 may, based on the user input received by the abstraction layer 130, transmit a normalized particular application programming interface call 206 to the particular resource platform 101 to cause the particular resource platform 101 to secure, for the user of the client device 102, the at least one resource 208 associated with the particular resource object 214. For example, the particular application programming interface call 206 can cause the platform 101 to reserve a particular machine at a particular time for utilization by the user of the client device
102. In another example, the particular application program-
ming interface call 206 can cause the platform 101 to post
a token to the platform 101. In another example, the par-
ticular application programming interface call 206 can cause
the platform 101 to update an existing patient in the platform
101. In another example, the particular application program-
ming interface call 206 can cause the platform 101 to create
a new patient in the platform 101.

In some embodiments, the particular application program-
ming interface call may be similar to in structure and
function as the customized application programming inter-
face call 206. The normalization layer 140 may, based on the
user input received by the abstraction layer 130, transmit a
normalized particular application programming interface
call 206 to the particular resource platform 101 to cause the
particular resource platform 101 to secure, for the user of the
client device 102, the at least one resource 208 associated
with the particular resource object 214. For example, the
particular application programming interface call 206 can
cause the platform 101 to reserve a particular machine at a
particular time for utilization by the user of the client device
102. In another example, the particular application program-
ming interface call 206 can cause the platform 101 to post
a token to the platform 101. In another example, the par-
ticular application programming interface call 206 can cause
the platform 101 to update an existing patient in the platform
101. In another example, the particular application program-
ming interface call 206 can cause the platform 101 to create
a new patient in the platform 101.

Figure 5:
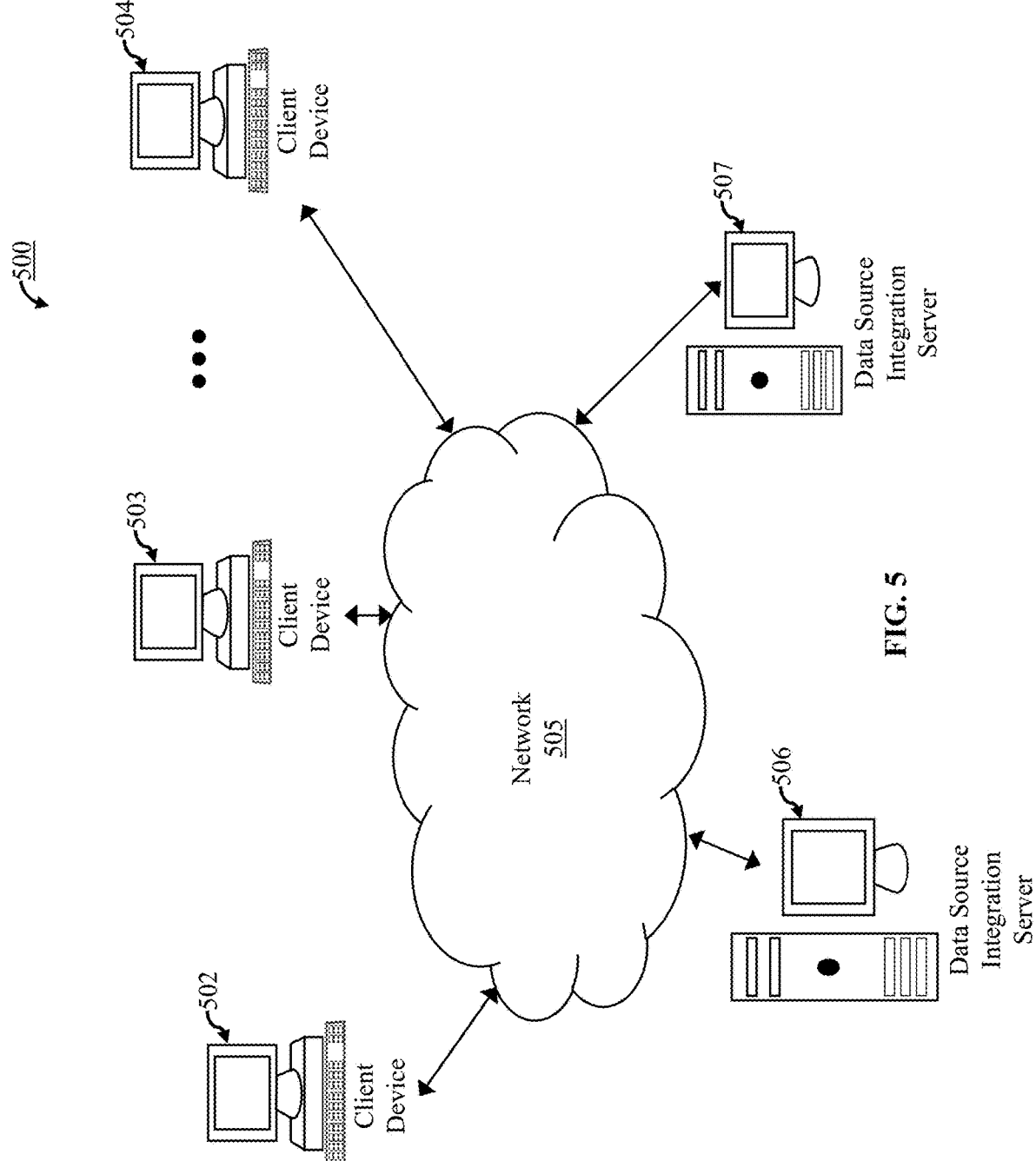
FIG. 5 depicts a block diagram of an exemplary computer-based system and platform for resource platform in accordance with one or more embodiments of the present disclosure.

FIG. 5 depicts a block diagram of an exemplary com-
puter-based system and platform 500 in accordance with one
or more embodiments of the present disclosure. However,
not all these components may be required to practice one or
more embodiments, and variations in the arrangement and
type of the components may be made without departing
from the spirit or scope of various embodiments of the
present disclosure. In some embodiments, the illustrative
computing devices and the illustrative computing compo-
nents of the exemplary computer-based system and platform
500 may be configured to manage a large number of
members and concurrent transactions, as detailed herein. In
some embodiments, the exemplary computer-based system
and platform 500 may be based on a scalable computer and
network architecture that incorporates varies strategies for
assessing the data, caching, searching, and/or database con-
nection pooling. An example of the scalable architecture is
an architecture that is capable of operating multiple servers.

In some embodiments, referring to FIG. 5, client device
502, client device 503 through client device 504 (e.g.,
clients) of the exemplary computer-based system and plat-
form 500 may include virtually any computing device
capable of receiving and sending a message over a network
(e.g., cloud network), such as network 505, to and from
another computing device, such as servers 506 and 507, each
other, and the like. In some embodiments, the client devices
502 through 504 may be personal computers, multiprocessor
systems, microprocessor-based or programmable consumer
electronics, network PCs, and the like. In some embodi-
ments, one or more client devices within client devices 502
through 504 may include computing devices that typically
connect using a wireless communications medium such as
cell phones, smart phones, pagers, walkie talkies, radio
frequency (RF) devices, infrared (IR) devices, citizens band
radio, integrated devices combining one or more of the
preceding devices, or virtually any mobile computing
device, and the like. In some embodiments, one or more client devices within client devices 502 through 504 may be
devices that are capable of connecting using a wired or
wireless communication medium such as a PDA, POCKET
PC, wearable computer, a laptop, tablet, desktop computer,
a netbook, a video game device, a pager, a smart phone, an
ultra-mobile personal computer (UMPC), and/or any other
device that is equipped to communicate over a wired and/or
wireless communication medium (e.g., NFC, RFID, NBIOT,
3G, 4G, 5G, GSM, GPRS, WiFi, WiMAX, CDMA, OFDM,
OFDMA, LTE, satellite, ZigBee, etc.). In some embodi-
ments, one or more client devices within client devices 502
through 504 may include may run one or more applications,
such as Internet browsers, mobile applications, voice calls,
video games, videoconferencing, and email, among others.
In some embodiments, one or more client devices within
client devices 502 through 504 may be configured to receive
and to send web pages, and the like. In some embodiments,
an exemplary specifically programmed browser application
of the present disclosure may be configured to receive and
display graphics, text, multimedia, and the like, employing
virtually any web based language, including, but not limited
to Standard Generalized Markup Language (SMGL), such
as Hypertext Markup Language (HTML), a wireless appli-
cation protocol (WAP), a Handheld Device Markup Lan-
guage (HDML), such as Wireless Markup Language
(WML), WMLScript, XML, JavaScript, and the like. In
some embodiments, a client device within client devices 502
through 504 may be specifically programmed by either Java,
.Net, QT, C, C++, Python, PHP and/or other suitable pro-
gramming language. In some embodiment of the device
software, device control may be distributed between mul-
tiple standalone applications. In some embodiments, soft-
ware components/applications can be updated and rede-
ployed remotely as individual units or as a full software
suite. In some embodiments, a client device may periodi-
cally report status or send alerts over text or email. In some
embodiments, a client device may contain a data recorder
which is remotely downloadable by the user using network
protocols such as FTP, SSH, or other file transfer mecha-
nisms. In some embodiments, a client device may provide
several levels of user interface, for example, advance user,
standard user. In some embodiments, one or more client
devices within client devices 502 through 504 may be
specifically programmed include or execute an application
to perform a variety of possible tasks, such as, without
limitation, messaging functionality, browsing, searching,
playing, streaming, or displaying various forms of content,
including locally stored or uploaded messages, images and/
or video, and/or games.

In some embodiments, the exemplary network 505 may
provide network access, data transport and/or other services
to any computing device coupled to it. In some embodi-
ments, the exemplary network 505 may include and imple-
ment at least one specialized network architecture that may
be based at least in part on one or more standards set by, for
example, without limitation, Global System for Mobile
communication (GSM) Association, the Internet Engineer-
ing Task Force (IETF), and the Worldwide Interoperability
for Microwave Access (WiMAX) forum. In some embodi-
ments, the exemplary network 505 may implement one or
more of a GSM architecture, a General Packet Radio Service
(GPRS) architecture, a Universal Mobile Telecommunica-
tions System (UMTS) architecture, and an evolution of
UMTS referred to as Long Term Evolution (LTE). In some
embodiments, the exemplary network 505 may include and
implement, as an alternative or in conjunction with one or
more of the above, a WiMAX architecture defined by the WiMAX forum. In some embodiments and, optionally, in combination of any embodiment described above or below, the exemplary network 505 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 505 may be transmitted based at least in part on one of more communication modes such as but not limited to: NFC, RFID, Narrow Band Internet of Things (NBIOT), ZigBee, 3G, 4G, 5G, GSM, GPRS, Wi-Fi, WiMAX, CDMA, OFDM, OFDMA, LTE, satellite and any combination thereof. In some embodiments, the exemplary network 505 may also include mass storage, such as network attached storage (NAS), a storage area network (SAN), a content delivery network (CDN) or other forms of computer or machine-readable media.

In some embodiments, the exemplary server 506 or the exemplary server 507 may be a web server (or a series of servers) running a network operating system, examples of which may include but are not limited to Apache on Linux or Microsoft IIS (Internet Information Services). In some embodiments, the exemplary server 506 or the exemplary server 507 may be used for and/or provide cloud and/or network computing. Although not shown in FIG. 5, in some embodiments, the exemplary server 506 or the exemplary server 507 may have connections to external systems like email, SMS messaging, text messaging, ad content providers, etc. Any of the features of the exemplary server 506 may be also implemented in the exemplary server 507 and vice versa.

In some embodiments, one or more of the exemplary servers 506 and 507 may be specifically programmed to perform, in non-limiting example, as authentication servers, search servers, email servers, social networking services servers, Short Message Service (SMS) servers, Instant Messaging (IM) servers, Multimedia Messaging Service (MMS) servers, exchange servers, photo-sharing services servers, advertisement providing servers, financial/banking-related services servers, travel services servers, or any similarly suitable service-base servers for users of the client devices 501 through 504.

In some embodiments and, optionally, in combination of any embodiment described above or below, for example, one or more exemplary computing client devices 502 through 504, the exemplary server 506, and/or the exemplary server 507 may include a specifically programmed software module that may be configured to send, process, and receive information using a scripting language, a remote procedure call, an email, a tweet, Short Message Service (SMS), Multimedia Message Service (MMS), instant messaging (IM), an application programming interface, Simple Object Access Protocol (SOAP) methods, Common Object Request Broker Architecture (CORBA), HTTP (Hypertext Transfer Protocol), REST (Representational State Transfer), SOAP (Simple Object Transfer Protocol), MLLP (Minimum Lower Layer Protocol), or any combination thereof.

Figure 6:
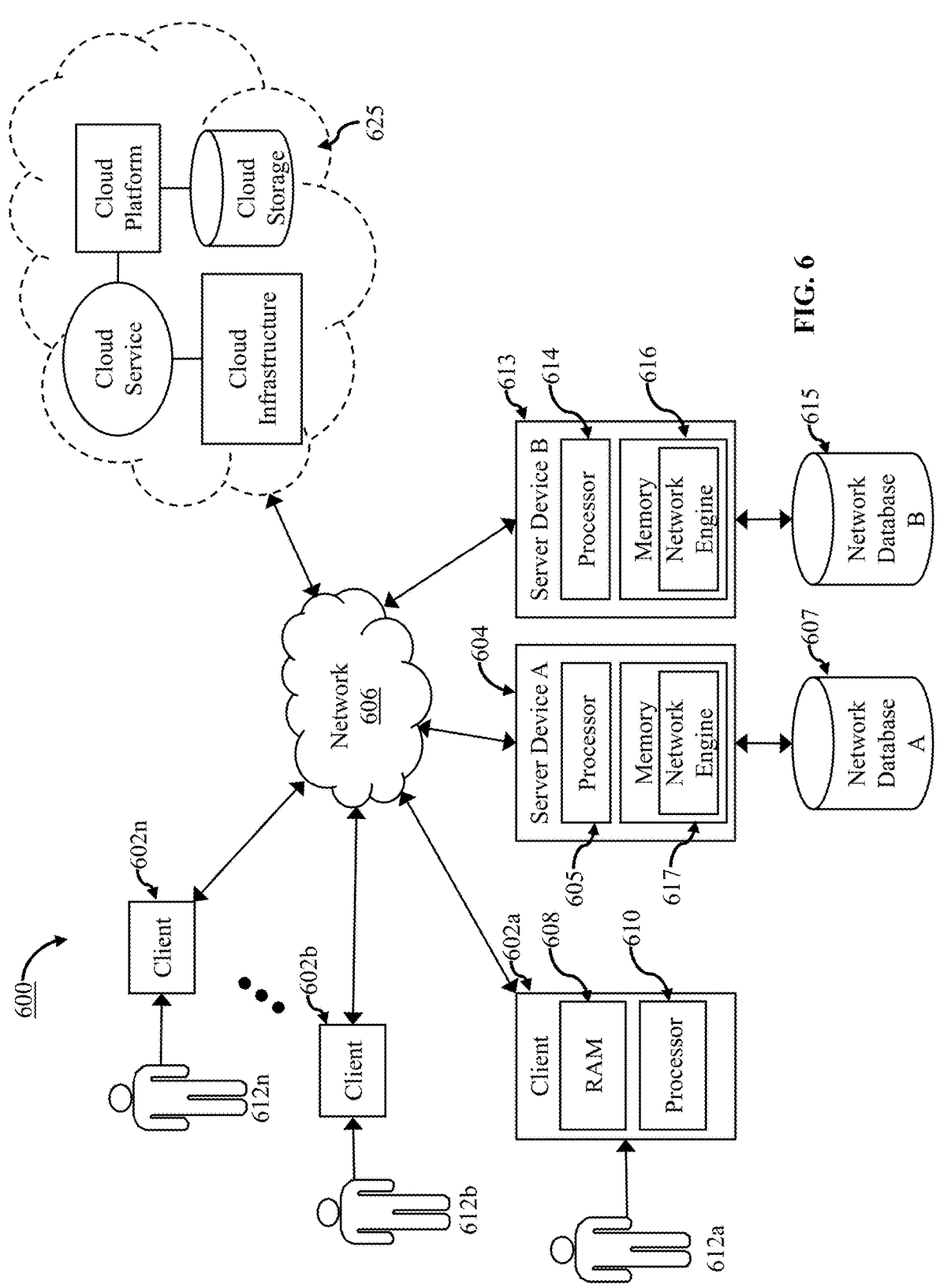
FIG. 6 depicts a block diagram of another exemplary computer-based system and platform for resource platform in accordance with one or more embodiments of the present disclosure.

FIG. 6 depicts a block diagram of another exemplary computer-based system and platform 600 in accordance with one or more embodiments of the present disclosure. However, not all these components may be required to practice one or more embodiments, and variations in the arrangement and type of the components may be made without departing from the spirit or scope of various embodiments of the present disclosure. In some embodiments, the client device 602a, client device 602b through client device 602n shown each at least includes a computer-readable medium, such as a random-access memory (RAM) 608 coupled to a processor 610 or FLASH memory. In some embodiments, the processor 610 may execute computer-executable program instructions stored in memory 608. In some embodiments, the processor 610 may include a microprocessor, an ASIC, and/or a state machine. In some embodiments, the processor 610 may include, or may be in communication with, media, for example computer-readable media, which stores instructions that, when executed by the processor 610, may cause the processor 610 to perform one or more steps described herein. In some embodiments, examples of computer-readable media may include, but are not limited to, an electronic, optical, magnetic, or other storage or transmission device capable of providing a processor, such as the processor 610 of client device 602a, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape, or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, etc.

In some embodiments, client devices 602a through 602n may also comprise several external or internal devices such as a mouse, a CD-ROM, DVD, a physical or virtual keyboard, a display, or other input or output devices. In some embodiments, examples of client devices 602a through 602n (e.g., clients) may be any type of processor-based platforms that are connected to a network 606 such as, without limitation, personal computers, digital assistants, personal digital assistants, smart phones, pagers, digital tablets, laptop computers, Internet appliances, and other processor-based devices. In some embodiments, client devices 602a through 602n may be specifically programmed with one or more application programs in accordance with one or more principles/methodologies detailed herein. In some embodiments, client devices 602a through 602n may operate on any operating system capable of supporting a browser or browser-enabled application, such as Microsoft™, Windows™, and/or Linux. In some embodiments, client devices 602a through 602n shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 602a through 602n, user 612a, user 612b through user 612n, may communicate over the exemplary network 606 with each other and/or with other systems and/or devices coupled to the network 606. As shown in FIG. 6, exemplary server devices 604 and 613 may include processor 605 and processor 614, respectively, as well as memory 617 and memory 616, respectively. In some embodiments, the server devices 604 and 613 may be also coupled to the network 606. In some embodiments, one or more client devices 602a through 602n may be mobile clients.

In some embodiments, at least one database of exemplary databases 607 and 615 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 7:
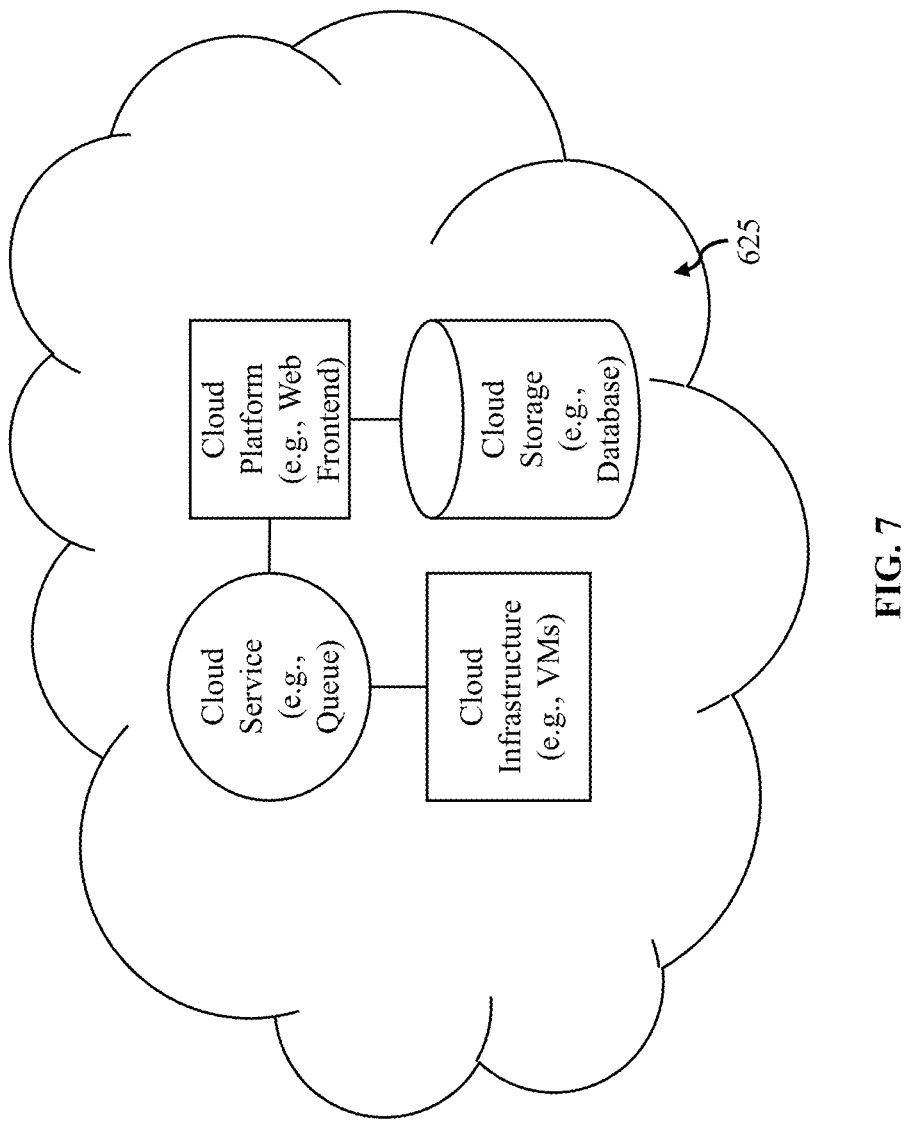
FIG. 7 depicts illustrative schematics of an exemplary implementation of the cloud computing/architecture(s) in which embodiments of a system for resource platform may be specifically configured to operate in accordance with some embodiments of the present disclosure.
Figure 8:
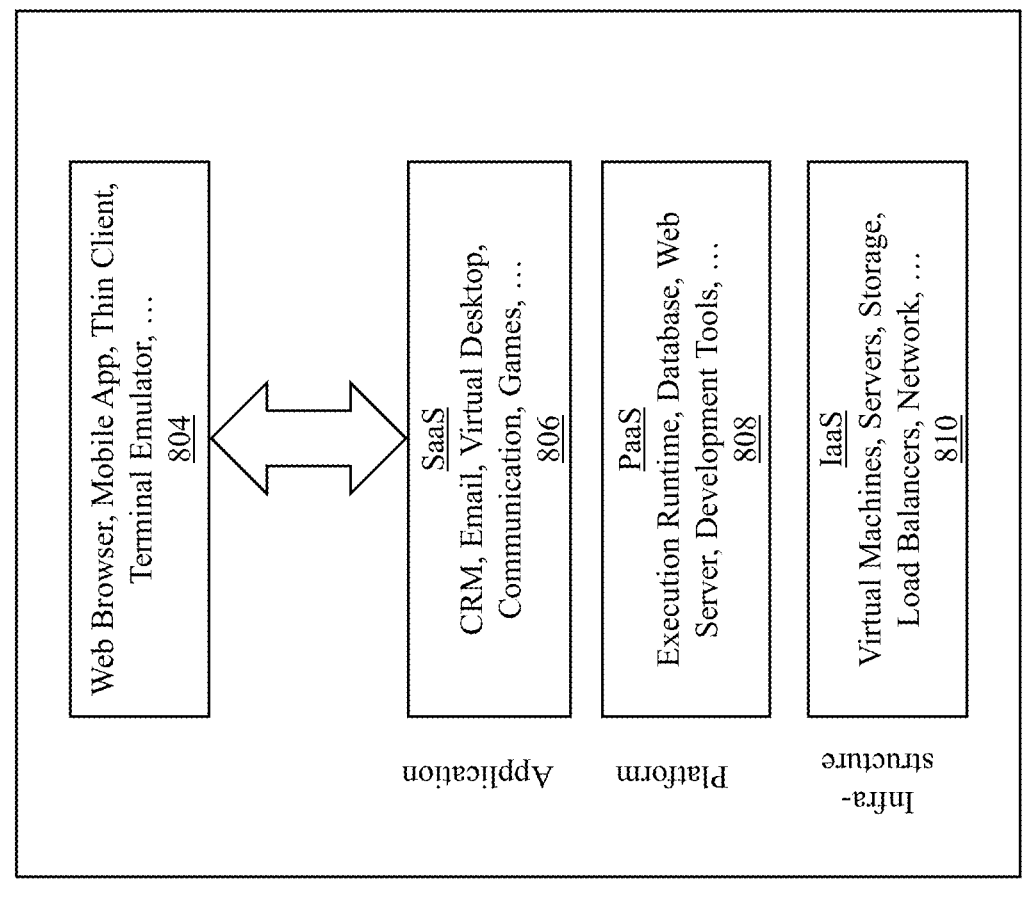
FIG. 8 depicts illustrative schematics of another exemplary implementation of the cloud computing/architecture(s) in which embodiments of a system for resource platform may be specifically configured to operate in accordance with some embodiments of the present disclosure.

In some embodiments, the exemplary inventive computer-based systems/platforms, the exemplary inventive computer-based devices, and/or the exemplary inventive computer-based components of the present disclosure may be specifically configured to operate in a cloud computing/architecture 625 such as, but not limiting to: infrastructure a service (IaaS) 810, platform as a service (PaaS) 808, and/or software as a service (SaaS) 806 using a web browser, mobile app, thin client, terminal emulator or other endpoint 804. FIGS. 7 and 8 illustrate schematics of exemplary implementations of the cloud computing/architecture(s) in which the exemplary inventive computer-based systems/platforms, the exemplary inventive computer-based devices, and/or the exemplary inventive computer-based components of the present disclosure may be specifically configured to operate.

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

As used herein, the term "runtime" corresponds to any behavior that is dynamically determined during an execution of a software application or at least a portion of software application.

In some embodiments, exemplary inventive, specially programmed computing systems and platforms with associated devices are configured to operate in the distributed network environment, communicating with one another over one or more suitable data communication networks (e.g., the Internet, satellite, etc.) and utilizing one or more suitable data communication protocols/modes such as, without limitation, IPX/SPX, X.25, AX.25, AppleTalk™, TCP/IP (e.g., HTTP), near-field wireless communication (NFC), RFID, Narrow Band Internet of Things (NBIOT), 3G, 4G, 5G, GSM, GPRS, Wi-Fi, WiMAX, CDMA, satellite, ZigBee, and other suitable communication modes.

The material disclosed herein may be implemented in software or firmware or a combination of them or as instructions stored on a machine-readable medium, which may be read and executed by one or more processors. A machine-readable medium may include any medium and/or mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical, or other forms of propagated signals (e.g., carrier waves, infrared signals, digital signals, etc.), and others.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores," may be stored on a tangible, machine readable medium and supplied to various customers or manufacturing facilities to load into the fabrication machines that make the logic or processor. Of note, various embodiments described herein may, of course, be implemented using any appropriate hardware and/or computing software languages (e.g., C++, Objective-C, Swift, Java, JavaScript, Python, Perl, QT, etc.).

In some embodiments, one or more of illustrative computer-based systems or platforms of the present disclosure may include or be incorporated, partially or entirely into at least one personal computer (PC), laptop computer, ultra-laptop computer, tablet, touch pad, portable computer, hand-held computer, palmtop computer, personal digital assistant (PDA), cellular telephone, combination cellular telephone/PDA, television, smart device (e.g., smart phone, smart tablet or smart television), mobile internet device (MID), messaging device, data communication device, and so forth.

As used herein, term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

In some embodiments, as detailed herein, one or more of the computer-based systems of the present disclosure may obtain, manipulate, transfer, store, transform, generate, and/or output any digital object and/or data unit (e.g., from inside and/or outside of a particular application) that can be in any suitable form such as, without limitation, a file, a contact, a task, an email, a message, a map, an entire application (e.g., a calculator), data points, and other suitable data. In some embodiments, as detailed herein, one or more of the computer-based systems of the present disclosure may be implemented across one or more of various computer platforms such as, but not limited to: (1) FreeBSD, NetBSD, OpenBSD; (2) Linux; (3) Microsoft Windows™; (4) Open VMS™; (5) OS X (MacOS™); (6) UNIX™; (7) Android; (8) iOS™; (9) Embedded Linux; (10) Tizen™; (11) WebOS™; (12) Adobe AIR™; (13) Binary Runtime Environment for Wireless (BREW™); (14) Cocoa™ (API); (15) Cocoa™ Touch; (16) Java™ Platforms; (17) JavaFX™; (18) QNX™; (19) Mono; (20) Google Blink; (21) Apple Web Kit; (22) Mozilla Gecko™; (23) Mozilla XUL; (24).NET Framework; (25) Silverlight™; (26) Open Web Platform; (27) Oracle Database; (28) Qt™; (29) SAP NetWeaver™; (30) Smartface™; (31) Vexi™; (32) Kubernetes™ and (33) Windows Runtime (WinRT™) or other suitable computer platforms or any combination thereof. In some embodiments, illustrative computer-based systems or platforms of the present disclosure may be configured to utilize hard-wired circuitry that may be used in place of or in combination with software instructions to implement features consistent with principles of the disclosure. Thus, implementations consistent with principles of the disclosure are not limited to any specific combination of hardware circuitry and software. For example, various embodiments may be embodied in many ways as a software component such as, without limitation, a stand-alone software package, a combination of software packages, or it may be a software package incorporated as a "tool" in a larger software product.

For example, exemplary software specifically programmed in accordance with one or more principles of the present disclosure may be downloadable from a network, for example, a website, as a stand-alone product or as an add-in package for installation in an existing software application. For example, exemplary software specifically programmed in accordance with one or more principles of the present disclosure may also be available as a client-server software application, or as a web-enabled software application. For example, exemplary software specifically programmed in accordance with one or more principles of the present disclosure may also be embodied as a software package installed on a hardware device.

In some embodiments, illustrative computer-based systems or platforms of the present disclosure may be configured to handle numerous concurrent users that may be, but is not limited to, at least 100 (e.g., but not limited to, 100-999), at least 1,000 (e.g., but not limited to, 1,000-9,999), at least 10,000 (e.g., but not limited to, 10,000-99,999), at least 100,000 (e.g., but not limited to, 100,000-999,999), at least 1,000,000 (e.g., but not limited to, 1,000,000-9,999,999), at least 10,000,000 (e.g., but not limited to, 10,000,000-99,999,999), at least 100,000,000 (e.g., but not limited to, 100,000,000-999,999,999), at least 1,000,000,000 (e.g., but not limited to, 1,000,000,000-999,999,999,999), and so on.

In some embodiments, illustrative computer-based systems or platforms of the present disclosure may be configured to output to distinct, specifically programmed graphical user interface implementations of the present disclosure (e.g., a desktop, a web app., etc.). In various implementations of the present disclosure, a final output may be displayed on a displaying screen which may be, without limitation, a screen of a computer, a screen of a mobile device, or the like. In various implementations, the display may be a holographic display. In various implementations, the display may be a transparent surface that may receive a visual projection. Such projections may convey various forms of information, images, or objects. For example, such projections may be a visual overlay for a mobile augmented reality (MAR) application.

In some embodiments, illustrative computer-based systems or platforms of the present disclosure may be configured to be utilized in various applications which may include, but not limited to, gaming, mobile-device games, video chats, video conferences, live video streaming, video streaming and/or augmented reality applications, mobile-device messenger applications, and others similarly suitable computer-device applications.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

In some embodiments, the illustrative computer-based systems or platforms of the present disclosure may be configured to securely store and/or transmit data by utilizing one or more of encryption techniques (e.g., private/public key pair, Triple Data Encryption Standard (3DES), block cipher algorithms (e.g., IDEA, RC2, RC5, CAST and Skipjack), cryptographic hash algorithms (e.g., MD5, RIPEMD-160, RTR0, SHA-1, SHA-2, Tiger (TTH), WHIRLPOOL, RNGs).

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session or can refer to an automated software application which receives the data and stores or processes the data.

The examples are, of course, illustrative, and not restrictive.

At least some aspects of the present disclosure will now be described with reference to the following numbered clauses.

Clause 1. A system comprising:

at least one interface gateway configured to interface with at least one client device and a plurality of resource platforms, the at least one interface gateway comprising a resource orchestrator comprising at least one processor in communication with at least one non-transitory computer-readable medium having software instructions stored thereon, wherein, upon execution of the software instructions, the at least one processor is configured to:

generate an abstracted query about a plurality of resources managed by the plurality of resource platforms;

wherein the abstracted query is for at least:

each respective resource of the plurality of resources, an availability of each respective resource of the plurality of resources, and a capability of each respective resource of the plurality of resources;

identify a plurality of application programming interfaces maintained by a normalization layer for querying the plurality of resource platforms about the plurality of resources managed by the plurality of resource platforms;

wherein the plurality of application programming interfaces are defined by a plurality of resource selection questionnaire templates specific to each respective resource platform of the plurality of resource platforms;

generate a respective normalized application programming interface call to each respective resource platform by modifying the abstracted query for each respective resource platform of the plurality of resource platforms based on each respective application programming interface of the plurality of application programming interfaces;

store, responsive to the respective normalized application programming interface call to each of the plurality of resource platforms, in a resource cache, a plurality of resource objects for each resource platform, wherein each of the plurality of resource objects that represent a respective resource of the plurality of resources managed by the plurality of resource platforms comprise:

an availability property indicating the availability of the respective resource, and a capability property indicating the capability of the respective resource;

receive, from the at least one client device, a resource request representing at least one request for at least one resource of the plurality of resources;

wherein the resource request comprises:

at least one user attribute associated with a user, and at least one resource request attribute defining at least one requested capability;

access the resource cache comprising the plurality of resource objects representing the plurality of resources managed by the plurality of resource platforms;

determine at least one particular resource property representing at least one particular capability that corresponds to:

the at least one user attribute, and the at least one requested capability defined by the at least one resource request attribute;

determine a particular resource object of the plurality of resource objects in the resource cache, the particular resource object comprising the at least one particular capability;

wherein the particular resource object represents a particular resource for the resource request;

determine a particular resource platform associated with the particular resource object;

transmit to the at least one client device, in real-time, a particular plurality of resource selection questionnaire templates specific to the particular resource platform so as to enable the at least one client device to:

display the particular plurality of resource selection questionnaire templates, and return at least one user input associated with the particular plurality of resource selection questionnaire templates;

determine, based on the at least one user input, a particular availability of the particular resource object; and generate, based on a particular application programming interface of the particular resource platform and the particular availability of the particular resource object, a particular application programming interface call comprising at least one resource selection configured to cause the particular resource platform to secure, for the user, the at least one resource associated with the particular resource object.

Clause 2. A method comprising:

generating, by at least one processor of a resource orchestrator of at least one interface gateway configured to interface with at least one client device and a plurality of resource platforms, an abstracted query about a plurality of resources managed by the plurality of resource platforms;

wherein the abstracted query is for at least:

51 each respective resource of the plurality of resources, an availability of each respective resource of the plurality of resources, and
   a capability of each respective resource of the plurality of resources;
identifying, by the at least one processor, a plurality of application programming interfaces maintained by a normalization layer for querying the plurality of resource platforms about the plurality of resources managed by the plurality of resource platforms;
   wherein the plurality of application programming interfaces are defined by a plurality of resource selection questionnaire templates specific to each respective resource platform of the plurality of resource platforms;
generating, by the at least one processor, a respective normalized application programming interface call to each respective resource platform by modifying the abstracted query for each respective resource platform of the plurality of resource platforms based on each respective application programming interface of the plurality of application programming interfaces;
storing, by the at least one processor, responsive to the respective normalized application programming interface call to each of the plurality of resource platforms, in a resource cache, a plurality of resource objects for each resource platform,
   wherein each of the plurality of resource objects that represent a respective resource of the plurality of resources managed by the plurality of resource platforms comprise:
      an availability attribute indicating the availability of the respective resource, and
      a capability attribute indicating the capability of the respective resource;
receiving, by the at least one processor, from the at least one client device, a resource request representing at least one request for at least one resource of the plurality of resources;
   wherein the resource request comprises:
      at least one user attribute associated with a user, and
      at least one resource request attribute defining at least one requested capability;
accessing, by the at least one processor, the resource cache comprising the plurality of resource objects representing the plurality of resources managed by the plurality of resource platforms;
determining, by the at least one processor, at least one particular resource attribute representing at least one particular capability that corresponds to:
   the at least one user attribute, and
   the at least one requested capability defined by the at least one resource request attribute;
determining, by the at least one processor, a particular resource object of the plurality of resource objects in the resource cache, the particular resource object comprising the at least one particular capability;
   wherein the particular resource object represents a particular resource for the resource request;
determining, by the at least one processor, a particular resource platform associated with the particular resource object;
transmit to the at least one client device, in real-time, a particular plurality of resource selection questionnaire templates specific to the particular resource platform so as to enable the at least one client device to:

52 display the particular plurality of resource selection questionnaire templates, and
   return, to the at least one processor, at least one user input associated with the particular plurality of resource selection questionnaire templates;
determining, by the at least one processor, based on the at least one user input, a particular availability of the particular resource object; and
generating, by the at least one processor, based on a particular application programming interface of the particular resource platform and the particular availability of the particular resource object, a particular application programming interface call comprising at least one resource selection configured to cause the particular resource platform to secure, for the user, the at least one resource associated with the particular resource object.

Clause 3. The system and/or method of any of clauses 1 and/or 2, wherein identifying the plurality of application programming interfaces comprises identifying three application programming interfaces for each of the plurality of resource platforms.

Clause 4. The system and/or method of any of clauses 1 and/or 2, wherein storing the plurality of resource objects comprises:
   receive, responsive to the respective normalized application programming interface call to each of the plurality of resource platforms, an unstructured response from each of the plurality of resource platforms,
      wherein the unstructured response is indicative of at least:
         the respective resource,
         the availability of the respective resource, and
         the capability of the respective resource; and
   generate, based on respective mapping identifiers for each respective resource platform of the plurality of resource platforms, the plurality of resource objects for storage in the resource cache using the respective mapping identifiers to map the unstructured response to the plurality of resource objects,
      wherein each of the plurality of resource objects that represent the plurality of resources managed by the plurality of resource platforms comprise:
         a respective resource property mapped to the respective resource,
         the availability property mapped to the availability of the respective resource, and
         the capability property mapped to the capability of the respective resource.

Clause 5. The system and/or method of any of clauses 1, 2, and/or 4, further comprising:
   determine, for each resource platform, the plurality of resource objects associated with the abstracted query based at least in part on the respective mapping identifiers;
   determine a set of additional application programming interface fields in each respective normalized application programming interface call;
      wherein the set of additional application programming interface fields are in addition to a set of abstracted query fields of the abstracted query;
      wherein the set of abstracted query fields define each respective resource of the plurality of resources;
   determine a set of additional application programming interface data for each respective normalized application programming interface call to populate the set of additional application programming interface fields based at least in part on the plurality of resource objects associated with the abstracted query; and generate the respective normalized application programming interface call to each respective resource platform by modifying the abstracted query for each respective resource platform of the plurality of resource platforms to include the set of additional application programming interface fields comprising the set of additional application programming interface data of each respective normalized application programming interface call.

Clause 6. The system and/or method of any of clauses 1 and/or 2, further comprising:

generate, periodically for each resource platform of the plurality of resource platforms, according to at least one refresh period, at least one subsequent abstracted query configured to synchronize the plurality of resource objects with the plurality of resource platforms;

generate, based on the at least one refresh period, at least one subsequent respective normalized application programming interface call to each respective resource platform by modifying the at least one subsequent abstracted query for each respective resource platform of the plurality of resource platforms based on each respective application programming interface of the plurality of application programming interfaces; and storing, responsive to the at least one subsequent respective normalized application programming interface call to each of the plurality of resource platforms, in the resource cache, a plurality of refreshed resource objects for each resource platform, wherein the plurality of refreshed resource objects comprises an up-to-date record of each resource of the plurality of resources managed by the plurality of resource platforms, comprising:

an updated availability property indicating a current availability of the respective resource, and an updated capability property indicating a current capability of the respective resource.

Clause 7. The system and/or method of any of clauses 1, 2, and/or 6, wherein the at least one refresh period comprises one day.

Clause 8. The system and/or method of any of clauses 1, 2, and/or 6, wherein the plurality of refreshed resource objects comprises the up-to-date record for changed resources of the plurality of resources.

Clause 9. The system and/or method of any of clauses 1, 2, and/or 6, wherein the plurality of refreshed resource objects comprises the up-to-date record for all the plurality of resources.

Clause 10. The system and/or method of any of clauses 1 and/or 2, wherein the plurality of resource platforms comprises a plurality of electronic health record (EHR) integrations.

Clause 11. The system and/or method of any of clauses 1 and/or 2, wherein the plurality of resources comprises a plurality of healthcare providers.

Publications cited throughout this document are hereby incorporated by reference in their entirety. While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

The invention claimed is:

1. A system comprising:

at least one processor configured to interface with at least one client device and a plurality of resource platforms, wherein, upon execution of software instructions, the at least one processor is configured to:

generate an abstracted query about a plurality of resources managed by at least one resource platform;

wherein the abstracted query is for at least:

each respective resource of the plurality of resources, an availability of each respective resource of the plurality of resources, and a capability of each respective resource of the plurality of resources;

identify at least one application programming interface maintained by a normalization layer for querying at least one resource platform about the plurality of resources;

wherein the at least one application programming interface comprises a structure specific to the at least one resource platform;

generate at least one normalized application programming interface call to the at least one resource platform based on the abstracted query and the at least one application programming interface; and receive, responsive to the at least one normalized application programming interface call, at least one response from the at least one resource platforms.

2. The system of claim 1, wherein, upon execution of software instructions, the at least one processor is further configured to:

receive, responsive to the at least one normalized application programming interface call to the at least one resource platform, at least one unstructured response from the at least one resource platform; and generate, based on at least one mapping identifiers for the at least one resource platform, at least one resource object associated with the abstracted query for storage in a resource cache using the at least one mapping identifier to map the at least one unstructured response to the at least one resource object.

3. The system of claim 2, wherein the at least one unstructured response is indicative of at least: the respective resource, the availability of the respective resource, and the capability of the respective resource.

4. The system of claim 2, wherein each of a plurality of resource objects that represent the plurality of resources managed by the plurality of resource platforms comprise:

a respective resource property mapped to the respective resource, an availability property mapped to the availability of the respective resource, and a capability property mapped to the capability of the respective resource.

5. The system of claim 1, wherein, upon execution of software instructions, the at least one processor is further configured to: store, responsive to the at least one normalized application programming interface call to the at least one resource platform, in a resource cache, a plurality of resource objects, wherein each of the plurality of resource objects represents a respective resource of the plurality of resources managed by the at least one resource platform; and wherein each of the plurality of resource objects comprises: an availability property indicating the availability of the respective resource, and a capability property indicating the capability of the respective resource.

6. The system of claim 1, wherein, upon execution of software instructions, the at least one processor is further configured to:

receive, from the at least one client device, a resource request representing at least one request for the at least one resource;

access a resource cache comprising a plurality of resource objects representing the plurality of resources managed by the plurality of resource platforms;

determine a particular resource object of the plurality of resource objects in the resource cache matching to the resource request;

determine a particular resource platform associated with the particular resource object; and generate, based on a particular application programming interface of the particular resource platform, a particular application programming interface call comprising at least one resource selection configured to cause the particular resource platform to secure, for a user, the at least one resource associated with the particular resource object.

7. The system of claim 6, wherein, upon execution of software instructions, the at least one processor is further configured to:

transmit to the at least one client device, in real-time, a particular plurality of resource selection questionnaire templates specific to the particular resource platform so as to enable the at least one client device to:

display the particular plurality of resource selection questionnaire templates, and return at least one user input associated with the particular plurality of resource selection questionnaire templates; and determine, based on the at least one user input, a particular availability of the particular resource object.

8. The system of claim 1, wherein the at least one processor is further configured to:

generate, periodically for the at least one resource platform, according to at least one refresh period, at least one subsequent abstracted query configured to synchronize a plurality of resource objects with the at least one resource platform, the plurality of resource objects representing the plurality of resources;

generate, based on the at least one refresh period, at least one subsequent respective normalized application programming interface call to the at least one resource platform by modifying the at least one subsequent abstracted query for the at least one resource platform based on the at least one application programming interface; and store, responsive to the at least one subsequent respective normalized application programming interface call to the at least one resource platform, in a resource cache, a plurality of refreshed resource objects for the at least one resource platform, wherein the plurality of refreshed resource objects comprises an up-to-date record of each resource of the plurality of resources managed by the at least one resource platform, comprising:

an updated availability property indicating a current availability of the respective resource, and an updated capability property indicating a current capability of the respective resource.

9. The system of claim 8, wherein the plurality of refreshed resource objects comprises the up-to-date record for changed resources of the plurality of resources.

10. The system of claim 1, wherein the at least one resource platform comprises at least one electronic health record (EHR) integration.

11. A method comprising:

generating, by at least one processor, an abstracted query about a plurality of resources managed by at least one resource platform;

wherein the abstracted query is for at least:

each respective resource of the plurality of resources, an availability of each respective resource of the plurality of resources, and a capability of each respective resource of the plurality of resources;

identifying, by the at least one processor, at least one application programming interface maintained by a normalization layer for querying at least one resource platform about the plurality of resources;

wherein the at least one application programming interface comprises a structure specific to the at least one resource platform;

generating, by the at least one processor, at least one normalized application programming interface call to the at least one resource platform based on the abstracted query and the at least one application programming interface; and receiving, by the at least one processor, responsive to the at least one normalized application programming interface call, at least one response from the at least one resource platforms.

12. The method of claim 11, further comprising:

receiving, by the at least one processor, responsive to the at least one normalized application programming interface call to the at least one resource platform, at least one unstructured response from the at least one resource platform; and generating, by the at least one processor, based on at least one mapping identifiers for the at least one resource platform, at least one resource object associated with the abstracted query for storage in a resource cache using the at least one mapping identifier to map the at least one unstructured response to the at least one resource object.

13. The method of claim 12, wherein the at least one unstructured response is indicative of at least: the respective resource, the availability of the respective resource, and the capability of the respective resource.

14. The method of claim 12, wherein each of a plurality of resource objects that represent the plurality of resources managed by the plurality of resource platforms comprise:

a respective resource property mapped to the respective resource, an availability property mapped to the availability of the respective resource, and a capability property mapped to the capability of the respective resource.

15. The method of claim 11, further comprising: storing, by the at least one processor, responsive to the at least one normalized application programming interface call to the at least one resource platform, in a resource cache, a plurality of resource objects, wherein each of the plurality of resource objects represents a respective resource of the plurality of resources managed by the at least one resource platform; and wherein each of the plurality of resource objects comprises: an availability property indicating the availability of the respective resource, and a capability property indicating the capability of the respective resource.

16. The method of claim 11, further comprising:

receiving, by the at least one processor, from the at least one client device, a resource request representing at least one request for the at least one resource;

accessing, by the at least one processor, a resource cache comprising a plurality of resource objects representing the plurality of resources managed by the plurality of resource platforms;

determining, by the at least one processor, a particular resource object of the plurality of resource objects in the resource cache matching to the resource request;

determining, by the at least one processor, a particular resource platform associated with the particular resource object; and generating, by the at least one processor, based on a particular application programming interface of the particular resource platform, a particular application programming interface call comprising at least one resource selection configured to cause the particular resource platform to secure, for a user, the at least one resource associated with the particular resource object.

17. The method of claim 16, further comprising:

transmitting, by the at least one processor, to the at least one client device, in real-time, a particular plurality of resource selection questionnaire templates specific to the particular resource platform so as to enable the at least one client device to:

display the particular plurality of resource selection questionnaire templates, and return at least one user input associated with the particular plurality of resource selection questionnaire templates; and determining, by the at least one processor, based on the at least one user input, a particular availability of the particular resource object.

18. The method of claim 11, further comprising:

generating, by the at least one processor, periodically for the at least one resource platform, according to at least one refresh period, at least one subsequent abstracted query configured to synchronize a plurality of resource objects with the at least one resource platform, the plurality of resource objects representing the plurality of resources;

generating, by the at least one processor, based on the at least one refresh period, at least one subsequent respective normalized application programming interface call to the at least one resource platform by modifying the at least one subsequent abstracted query for the at least one resource platform based on the at least one application programming interface; and storing, by the at least one processor, responsive to the at least one subsequent respective normalized application programming interface call to the at least one resource platform, in a resource cache, a plurality of refreshed resource objects for the at least one resource platform, wherein the plurality of refreshed resource objects comprises an up-to-date record of each resource of the plurality of resources managed by the at least one resource platform, comprising:

an updated availability property indicating a current availability of the respective resource, and an updated capability property indicating a current capability of the respective resource.

19. The method of claim 18, wherein the plurality of refreshed resource objects comprises the up-to-date record for changed resources of the plurality of resources.

20. The method of claim 11, wherein the at least one resource platform comprises at least one electronic health record (EHR) integration.

* * * * *